US009155827B2

(12) United States Patent
Franano

(10) Patent No.: US 9,155,827 B2
(45) Date of Patent: Oct. 13, 2015

(54) SYSTEM AND METHOD TO INCREASE THE OVERALL DIAMETER OF VEINS

(75) Inventor: F. Nicholas Franano, Lenexa, KS (US)

(73) Assignee: FLOW FORWARD MEDICAL, INC., Olathe, KS (US)

(*) Notice: Subject to any disclaimer, the term of this patent is extended or adjusted under 35 U.S.C. 154(b) by 0 days.

(21) Appl. No.: 13/030,054

(22) Filed: Feb. 17, 2011

(65) Prior Publication Data
US 2011/0201990 A1 Aug. 18, 2011

Related U.S. Application Data

(60) Provisional application No. 61/305,508, filed on Feb. 17, 2010.

(51) Int. Cl.
A61M 5/00 (2006.01)
A61M 1/36 (2006.01)
A61M 1/10 (2006.01)
A61M 1/12 (2006.01)

(52) U.S. Cl.
CPC .............. *A61M 1/3655* (2013.01); *A61M 1/101* (2013.01); *A61M 1/1086* (2013.01); *A61M 1/12* (2013.01); *A61M 1/125* (2014.02); *A61M 1/367* (2013.01); *A61M 2206/10* (2013.01)

(58) Field of Classification Search
CPC ...... A61M 1/3655; A61M 1/367; A61M 1/10
USPC ............................................................ 604/9
See application file for complete search history.

(56) References Cited

U.S. PATENT DOCUMENTS

| 3,487,784 A | 1/1970 | Rafferty et al. |
| 3,864,055 A | 2/1975 | Kletschka et al. |
| 4,457,673 A | 7/1984 | Conley et al. |
| 4,507,048 A | 3/1985 | Belenger et al. |
| 4,557,673 A | 12/1985 | Chen et al. |
| 4,606,698 A | 8/1986 | Clausen et al. |
| 4,665,896 A | 5/1987 | LaForge et al. |
| 4,756,302 A | 7/1988 | Portner et al. |
| 4,898,518 A | 2/1990 | Hubbard et al. |
| 4,984,972 A | 1/1991 | Clausen et al. |
| 4,994,017 A | 2/1991 | Yozu |

(Continued)

FOREIGN PATENT DOCUMENTS

| EP | 1825872 A2 | 8/2007 |
| WO | 2009059371 A2 | 5/2009 |

OTHER PUBLICATIONS

Pries et al., Remodeling of Blood Vessels: Responses of Diameter and Wall Thickness to Hemodynamic and Metabolic Stimuli, Hypertension (2005), 46: 725-731.*

(Continued)

*Primary Examiner* — Philip R Wiest
*Assistant Examiner* — Ariana Zimbouski
(74) *Attorney, Agent, or Firm* — Polsinelli PC

(57) ABSTRACT

A system and method for increasing the speed of blood and wall shear stress (WSS) in a peripheral vein for a sufficient period of time to result in a persistent increase in the overall diameter and lumen diameter of the vein is provided. The method includes pumping blood at a desired rate and pulsatility. The pumping is monitored and adjusted, as necessary, to maintain the desired blood speed, WSS and pulsatility in the peripheral vein in order to optimize the rate and extent of dilation of the peripheral vein.

19 Claims, 15 Drawing Sheets

(56) References Cited

U.S. PATENT DOCUMENTS

| | | | |
|---|---|---|---|
| 5,006,104 A | 4/1991 | Smith et al. | |
| 5,017,103 A | 5/1991 | Dahl | |
| 5,162,102 A | 11/1992 | Nogawa et al. | |
| 5,290,236 A | 3/1994 | Mathewson | |
| 5,316,440 A | 5/1994 | Kijima et al. | |
| 5,324,177 A | 6/1994 | Golding et al. | |
| 5,399,074 A | 3/1995 | Nose et al. | |
| 5,509,908 A | 4/1996 | Hillstead | |
| D372,921 S | 8/1996 | Ijiri et al. | |
| 5,658,136 A | 8/1997 | Mendler | |
| 5,662,711 A * | 9/1997 | Douglas | 604/9 |
| 5,683,231 A | 11/1997 | Nakazawa et al. | |
| 5,713,730 A | 2/1998 | Nose et al. | |
| 5,766,207 A | 6/1998 | Potter et al. | |
| 5,803,720 A | 9/1998 | Ohara et al. | |
| 5,851,174 A | 12/1998 | Jarvik et al. | |
| 5,863,179 A | 1/1999 | Westphal et al. | |
| 5,890,883 A | 4/1999 | Golding et al. | |
| 5,894,011 A * | 4/1999 | Prosl et al. | 422/44 |
| 5,947,703 A | 9/1999 | Nojiri et al. | |
| 5,947,892 A | 9/1999 | Benkowski et al. | |
| 5,989,206 A | 11/1999 | Prosl et al. | |
| 6,015,272 A | 1/2000 | Antaki et al. | |
| 6,050,975 A | 4/2000 | Poirier | |
| 6,093,001 A | 7/2000 | Burgreen et al. | |
| 6,110,139 A | 8/2000 | Loubser | |
| 6,116,862 A | 9/2000 | Rau et al. | |
| 6,152,704 A | 11/2000 | Aboul-Hosn et al. | |
| 6,162,017 A | 12/2000 | Raible | |
| 6,183,220 B1 | 2/2001 | Ohara et al. | |
| 6,183,412 B1 | 2/2001 | Benkowski et al. | |
| 6,189,388 B1 | 2/2001 | Cole et al. | |
| 6,200,260 B1 | 3/2001 | Bolling | |
| 6,201,329 B1 | 3/2001 | Chen | |
| 6,217,541 B1 * | 4/2001 | Yu | 604/9 |
| 6,227,797 B1 | 5/2001 | Watterson et al. | |
| 6,227,817 B1 | 5/2001 | Paden | |
| 6,234,772 B1 | 5/2001 | Wampler et al. | |
| 6,244,835 B1 | 6/2001 | Antaki et al. | |
| 6,264,601 B1 | 7/2001 | Jassawalla et al. | |
| 6,299,575 B1 | 10/2001 | Bolling | |
| 6,346,071 B1 | 2/2002 | Mussivand | |
| 6,439,845 B1 | 8/2002 | Veres | |
| 6,447,265 B1 | 9/2002 | Antaki et al. | |
| 6,447,266 B2 | 9/2002 | Antaki et al. | |
| 6,652,447 B2 | 11/2003 | Benkowski et al. | |
| 6,688,861 B2 | 2/2004 | Wampler | |
| 6,692,318 B2 | 2/2004 | McBride | |
| 6,719,791 B1 | 4/2004 | Nusser et al. | |
| 6,742,999 B1 | 6/2004 | Nusser et al. | |
| 6,878,140 B2 | 4/2005 | Barbut | |
| 6,884,210 B2 | 4/2005 | Nose et al. | |
| 6,929,777 B1 | 8/2005 | Litwak et al. | |
| 6,969,345 B2 | 11/2005 | Jassawalla et al. | |
| 6,991,595 B2 | 1/2006 | Burke et al. | |
| 7,059,052 B2 | 6/2006 | Okamura et al. | |
| 7,138,776 B1 | 11/2006 | Gauthier et al. | |
| 7,160,242 B2 | 1/2007 | Yani | |
| 7,172,550 B2 | 2/2007 | Tsubouchi | |
| 7,229,474 B2 | 6/2007 | Hoffmann et al. | |
| 7,374,574 B2 | 5/2008 | Nuesser et al. | |
| 7,393,181 B2 | 7/2008 | McBride et al. | |
| 7,396,327 B2 | 7/2008 | Morello | |
| 7,467,929 B2 | 12/2008 | Nusser et al. | |
| 7,476,077 B2 | 1/2009 | Woodard et al. | |
| 7,485,104 B2 * | 2/2009 | Kieval | 604/9 |
| 7,491,163 B2 | 2/2009 | Viole et al. | |
| 7,494,477 B2 | 2/2009 | Rakhorst et al. | |
| 7,572,217 B1 | 8/2009 | Koenig et al. | |
| 7,575,423 B2 | 8/2009 | Wampler | |
| 7,578,782 B2 | 8/2009 | Miles et al. | |
| 7,588,530 B2 | 9/2009 | Heilman et al. | |
| 7,614,997 B2 | 11/2009 | Bolling | |
| 7,614,998 B2 | 11/2009 | Gross et al. | |
| 7,699,586 B2 | 4/2010 | LaRose et al. | |
| 7,736,296 B2 | 6/2010 | Siess et al. | |
| 7,762,977 B2 | 7/2010 | Porter et al. | |
| 2002/0026944 A1 | 3/2002 | Aboul-Hosn et al. | |
| 2003/0163078 A1 * | 8/2003 | Fallen et al. | 604/6.01 |
| 2004/0133173 A1 | 7/2004 | Edoga et al. | |
| 2004/0171905 A1 | 9/2004 | Yu et al. | |
| 2004/0186461 A1 | 9/2004 | Dimatteo | |
| 2004/0234397 A1 | 11/2004 | Wampler | |
| 2005/0033107 A1 | 2/2005 | Tsubouchi | |
| 2005/0085684 A1 | 4/2005 | Rakhorst et al. | |
| 2005/0113631 A1 * | 5/2005 | Bolling et al. | 600/16 |
| 2005/0277964 A1 | 12/2005 | Brenneman et al. | |
| 2006/0122552 A1 * | 6/2006 | O'Mahony | 604/6.11 |
| 2006/0142633 A1 | 6/2006 | Lane et al. | |
| 2006/0222533 A1 | 10/2006 | Reeves et al. | |
| 2007/0253842 A1 | 11/2007 | Horvath et al. | |
| 2008/0114339 A1 | 5/2008 | McBride et al. | |
| 2008/0124231 A1 | 5/2008 | Yaegashi | |
| 2008/0240947 A1 | 10/2008 | Allaire et al. | |
| 2008/0281250 A1 * | 11/2008 | Bergsneider et al. | 604/9 |
| 2009/0024072 A1 * | 1/2009 | Criado et al. | 604/9 |
| 2009/0156885 A1 | 6/2009 | Morello et al. | |
| 2010/0041939 A1 | 2/2010 | Siess | |
| 2015/0157787 A1 * | 6/2015 | Cully | A61M 5/158 604/6.05 |

OTHER PUBLICATIONS

Pries et al. (Remodeling of Blood Vessels: Responses of Diameter and Wall Thickness to Hemodynamic and Metabolic Stimuli, Hypertension. 2005; 46:725-731).*

Dimensions of Blood Vessels from Distributing Artery to Collecting Vein (Wiedeman, Circ Res. 1963;12:375-378).*

Characteristics of the response of the iliac artery to wall shear stress in the anaesthetized pig (Kelly et al., J Physiol 2007;582.2:731-743).*

Gujja et al.; "Interventional Therapies for Heart Failure"; SIS 2007 Yearbook; Chapter 13; (11 pages).

PCT/US2011/025331; International Search Report; mailed May 9, 2011; (2 pages).

PCT/US2013/055221; International Search Report and Written Opinion; mailed Feb. 3, 2014; (35 pages).

Bennett et al.; "Pump-induced Haemolysis: A Comparision of Short-term Ventricular Assist Devices"; Perfusion, Mar. 2004; vol. 19, No. 2; p. 108.

James et al.; "Evaluation of Hemolysis in the VentrAssist Implantable Rotary Blood Pump"; Artificial Organs; Jan. 2003; vol. 27; p. 110.

Kawahito et al.; "Hemolysis in Different Centrifugal Pumps"; Artificial Organs; Apr. 1997; vol. 21; No. 4; pp. 323-326.

* cited by examiner

SYSTEM AND METHOD TO INCREASE THE OVERALL DIAMETER OF VEINS

BACKGROUND OF THE INVENTION

1. Field of the Invention

The present invention relates to systems and methods for persistently increasing the overall diameter and the lumen diameter of veins in patients. Specifically, the present invention relates to systems and methods that utilize a blood pump to increase the blood speed and wall shear stress (WSS) on the endothelium of peripheral veins for a period of time that results in a persistent increase in the overall diameter and lumen diameter of those veins.

2. Background Information

Many patients with chronic kidney disease eventually progress to end-stage renal disease (ESRD) and need renal replacement therapy in order to remove fluid and waste products from their body and sustain their life. Most patients with ESRD needing renal replacement therapy receive hemodialysis. During hemodialysis, blood is removed from the circulatory system, cleansed in a hemodialysis machine, and then returned to the circulatory system. Surgeons create discrete "vascular access sites" that can be used to remove and return blood rapidly from ESRD patients. While major advances have been made in the hemodialysis machines themselves and other parts of the hemodialysis process, the creation of durable and reliable vascular access sites where blood can be removed and returned to patients during hemodialysis sessions has seen only modest improvement and remains the Achilles' heel of renal replacement therapy. This often results in sickness and death for ESRD patients and places a large burden on health care providers, payers, and public assistance programs worldwide.

Hemodialysis access sites generally come in three forms: arteriovenous fistulas (AVF), arteriovenous grafts (AVG), and catheters. Each type of site is susceptible to high rates of failure and complications, as described below.

An AVF is constructed surgically by creating a direct connection between an artery and vein. A functional wrist AVF is the longest-lasting, most desirable form of hemodialysis access, with a mean patency of about 3 years. The vein leading away from the connection is called the "outflow" vein. Dilation of the outflow vein is a critical component for an AVF to "mature" and become usable. It is widely believed that the rapid flow of blood in the outflow vein created by the AVF and the WSS it exerts on the endothelium of the vein is the major factor driving vein dilation. Unfortunately, approximately 80% of patients aren't eligible for AVF placement in the wrist, usually due to inadequate vein diameter. For eligible patients where AVF placement is attempted, the site is not usable without further intervention in about 50%-60% of cases, a problem known as "maturation failure". Small vessel diameter, especially small vein diameter, has been identified as an important factor in AVF maturation failure. The rapid appearance of aggressive vein wall scarring known as "intimal hyperplasia" has also been identified as an important factor in AVF maturation failure. It is generally believed that the turbulence created by the rapid flow of blood out of the artery and into the vein is a major factor causing this vein wall scarring. Some investigators also postulate that cyclic stretching of the vein caused by the entry of pulsatile arterial blood may also play a role in the stimulation of intimal hyperplasia and outflow vein obstruction in AVF. As such, there is a teaching that rapid flow is problematic, and attempts have been made to reduce flow in hemodialysis access sites by restricting lumen diameter by banding in order to minimize failure rates. At the current time, no method exists which preserves positive effects of flow-mediated dilation while eliminating the negative effects of vein wall scarring and obstruction. Not surprisingly, a patient newly diagnosed with ESRD and in need of hemodialysis has only a 50% chance of having a functional AVF within 6 months after starting hemodialysis. Those patients without a functional AVF are forced to dialyze with more costly forms of vascular access and are at a greater risk of complications, sickness, and death.

The second type of vascular access for hemodialysis is known as an arteriovenous graft (AVG). An AVG is constructed by placing a segment of synthetic conduit between an artery and vein, usually in the arm or leg. A portion of the synthetic conduit is placed immediately under the skin and used for needle access. More patients are eligible for AVGs, since veins not visible on the skin surface can be used for outflow, and the rate of early failure is much lower than for AVFs. Unfortunately, AVG mean primary patency is only about 4-6 months, mostly because aggressive intimal hyperplasia and scarring develops rapidly in the wall of the vein near the connection with the synthetic conduit, leading to stenosis and thrombosis. Similar to the situation with AVF failure, the rapid and turbulent flow of blood created by the AVG is thought to drive intimal hyperplasia and scarring in the wall of the outflow vein, often resulting in obstruction of the AVG. Some investigators also postulate that cyclic stretching of the vein caused by the entry of pulsatile arterial blood may also play a role in the formation of intimal hyperplasia and outflow vein obstruction in AVG. Although AVGs are less desirable than AVFs, about 25% of patients dialyze with an AVG, mostly because they are not eligible to receive an AVF.

Patients who are not able to get hemodialysis through an AVF or AVG must have a large catheter inserted in the neck, chest, or leg in order to receive hemodialysis. These catheters often become infected, placing the patient at high risk for sepsis and death. Patients with catheter sepsis usually require hospitalization, removal of the catheter, insertion of a temporary catheter, treatment with IV antibiotics, and then placement of a new catheter or other type of access site when the infection has cleared. Catheters are also susceptible to obstruction by thrombus and fibrin build-up around the tip. Hemodialysis catheters have a mean patency of about 6 months and are generally the least desirable form of hemodialysis access. Although catheters are less desirable than AVFs and AVG, about 20% of patients dialyze with a catheter, mostly because they have not yet been able to receive a functional AVF or AVG, or are not eligible to receive an AVF or AVG.

The problem of hemodialysis access site failure has received more attention recently as the number of ESRD patients undergoing routine hemodialysis has increased worldwide. In 2004, the Centers for Medicare & Medicaid Services (CMS) announced a "Fistula First" initiative to increase the use of AVFs in providing hemodialysis access for patients with end-stage renal failure. This major initiative is a response to published Medicare data showing that patients who dialyze with an AVF have reduced morbidity and mortality compared to patients with an AVG or a catheter. Costs associated with AVF patients are substantially lower than the costs associated with AVG patients in the first year of dialysis, and in subsequent years. The cost savings of a dialyzing with an AVF are even greater when compared to dialyzing with a catheter.

To be eligible for an AVF or AVG, patients must have a peripheral vein with a lumen diameter of at least 2.5 mm or 4 mm, respectively. However, there is currently no method for persistently increasing the overall diameter and lumen diameter of peripheral veins in ESRD patients who are ineligible for an AVF or AVG due to inadequate vein size. Consequently, patients with veins that are too small to attempt an AVF or AVG are forced to use less desirable forms of vascular access such as catheters. Similarly, there is currently no method of treatment for AVF maturation failure, which falls disproportionately on patients with small vein diameters. Thus, systems and methods for enlarging the overall diameter and lumen diameter of a vein prior to the creation of AVF or AVG are needed. The importance of this need is highlighted by a recent study demonstrating that ESRD patients who were forced to use less desirable forms of vascular access such as catheters had a substantially higher risk of becoming sick or dying when compared with patients who were able to use an AVF or AVG for hemodialysis.

There is also a need to persistently increase vein diameter for other patients, such as those with atherosclerotic blockage of peripheral arteries who are in need of peripheral bypass grafting. Patients with peripheral artery disease (PAD) who have an obstruction to blood flow in the arteries of the legs often suffer from claudication, skin ulceration, and tissue ischemia and many of these patients eventually require amputation of portions of the affected limb. In some of these patients, the obstruction can be relieved to an adequate degree by balloon angioplasty or the implantation of a vascular stent. In many patients, however, the obstruction is too severe for these types of minimally invasive therapies. Therefore, surgeons will often create a bypass graft that diverts blood around the obstructed arteries and restores adequate blood flow to the affected extremity. However, many patients in need of a peripheral bypass graft cannot use their own veins as bypass conduits due to inadequate vein diameter and are forced to use synthetic conduits made of materials such as polytetrafluoroethylene (PTFE, e.g. Gore-Tex) or polyethylene terephthalate (PET, e.g. Dacron). Studies have shown that using a patient's own veins as bypass conduits results in better long term patency than using synthetic bypass conduits made from materials such as PTFE or Dacron. The use of a synthetic bypass conduit increases the risk of stenosis in the artery at the distal end of the graft and thrombosis of the entire conduit, resulting in bypass graft failure and a recurrence or worsening of symptoms. Thus, systems and methods for increasing the overall diameter and lumen diameter of veins prior to the creation of bypass grafts are needed, especially for patients who are ineligible to use their own veins for the creation of a bypass graft due to inadequate vein diameter.

In view of the above, it will be apparent to those skilled in the art from this disclosure that there exists a need for a system and method for persistently increasing the lumen diameter and overall diameter of peripheral veins so that those veins can be used for the creation of hemodialysis access sites and bypass grafts. The invention described herein addresses this need in the art as well as other needs, which will become apparent to those skilled in the art from this disclosure.

SUMMARY OF THE INVENTION

The present invention includes methods of using a blood pump to increase the overall diameter and the lumen diameter of peripheral veins. Systems and methods are described wherein the wall shear stress (WSS) exerted on the endothelium of the peripheral vein is increased by placing a blood pump upstream of the peripheral vein for a period of time sufficient to result in dilation of the peripheral vein. The pump directs the blood into the peripheral vein preferably in a manner wherein the blood has reduced pulse pressure when compared with the pulse pressure of blood in a peripheral artery.

Studies have shown hemodynamic forces and changes in hemodynamic forces within veins play a vital role in determining the overall diameter and lumen diameter of those veins. For example, persistent increases in blood speed and WSS can lead to vein dilation, with the amount of dilation being dependent both on the level of increased blood speed and WSS and the time that the blood speed and WSS are elevated. The elevated blood speed and WSS are sensed by endothelial cells, which trigger signaling mechanisms that result in stimulation of vascular smooth muscle cells, attraction of monocytes and macrophages, and synthesis and release of proteases capable of degrading components of the extracellular matrix such as collagen and elastin. As such, the present invention relates to increasing blood speed and WSS for a period of time sufficient to result in vein remodeling and dilation, preferably for a period of time greater than seven days. The present invention also relates to methods of periodic adjustment of pump parameters to optimize vein remodeling and dilation.

Wall shear stress has been shown to be the key factor for blood vessel dilation in response to an increased blood flow. Assuming a Hagen-Poiseuille blood flow in the vessel (i.e. a laminar flow with a fully developed parabolic velocity profile), then WSS is given by the equation:

$WSS(\tau) = 4Q\mu/\pi R^3$, where:

Q=volume flow rate in mL/s
µ=viscosity of blood in units of poise
R=radius of vessel in cm
τ=wall shear stress in dynes/cm²

The systems and methods described herein increase the WSS level in a peripheral vein. Normal WSS for veins ranges between 0.076 Pa and 0.76 Pa. The systems and methods described herein increase the WSS level to a range between 0.76 Pa and 23 Pa, preferably to a range between 2.5 Pa and 7.5 Pa. Preferably, the WSS is increased for between 7 days and 84 days, or preferably between 7 and 42 days, to induce persistent dilation in the peripheral accepting vein such that veins that were initially ineligible for use as a hemodialysis access site or bypass graft due to a small vein diameter become usable. This can also be accomplished by intermittently increasing WSS during the treatment period, with intervening periods of normal WSS.

The systems and methods described herein also increase the speed of blood in peripheral veins and in certain instances, peripheral arteries. At rest, the mean speed of blood in the cephalic vein in humans is generally between 5-9 cm/s, while the speed of blood in the brachial artery is generally between 10-15 cm/s. For the systems and methods described herein, the mean speed of blood in the peripheral vein is increased to a range between 15 cm/s-100 cm/s, preferably to a range between 25 cm/s and 100 cm/s, depending on the diameter of peripheral accepting vein and the length of time the pumping of blood into the peripheral accepting vein is planned. Preferably, the mean blood speed is increased for between 7 days and 84 days, or preferably between 7 and 42 days, to induce persistent dilation in the peripheral accepting vein such that veins that were initially ineligible for use as a hemodialysis access site or bypass graft due to a small vein diameter become usable. This can also be accomplished by intermittently increasing mean blood speed during the treatment period, with intervening periods of normal mean blood speed.

A method of increasing the lumen diameter and overall diameter of a peripheral vein in a patient is set forth herein.

The method comprises performing a first procedure to access an artery or vein (the donating vessel) and a peripheral vein (the accepting vein) and connecting the donating vessel to the accepting vein with a pump system. The pump system is then activated to artificially direct blood from the donating vessel to the accepting vein. The method also includes monitoring the blood pumping process for a period of time. The method further includes adjusting the speed of the pump, the speed of the blood being pumped, or the WSS on the endothelium of the accepting vein and monitoring the pumping process again. After a period of time has elapsed to allow for vein dilation, the diameter of the accepting vein is measured to determine if adequate persistent increase in the overall diameter and lumen diameter of the accepting vein has been achieved and the pumping process is adjusted again, as necessary, When adequate amount of persistent increase in the overall diameter and lumen diameter of the accepting vein has been achieved, a second surgery is performed to remove the pump. A hemodialysis access site (such as an AVF or AVG) or bypass graft can be created at this time, or a later time, using at least a portion of the persistently enlarged accepting vein.

In one embodiment, a surgical procedure is performed to expose segments of two veins. One end of a first synthetic conduit is "fluidly" connected (i.e. joined lumen to lumen to permit fluid communication therebetween) to the vein where blood is to be removed (the donating vein). The other end of the first synthetic conduit is fluidly connected to the inflow port of a pump. One end of a second synthetic conduit is fluidly connected to the vein where blood is to be directed (the accepting vein). The other end of the second synthetic conduit is fluidly connected to the outflow port of the same pump. Deoxygenated blood is pumped from the donating vein to the accepting vein until the vein has persistently dilated to the desired overall diameter and lumen diameter. The term "persistently dilated" is used herein to mean that even if a pump is turned off an increase in overall diameter or lumen diameter of a vessel can still be demonstrated, when compared to the diameter of the vein prior to the period of blood pumping. That is, the vessel has become larger independent of the pressure generated by the pump. Once the desired amount of persistent vein enlargement has occurred, a second surgical procedure is performed to remove the pump and synthetic conduits. A hemodialysis access site (such as an AVF or AVG) or bypass graft can be created at this time, or a later time, using at least a portion of the persistently enlarged accepting vein. In this embodiment, the pump port may be fluidly connected directly to the donating vein or the accepting vein without using an interposed synthetic conduit. In a variation of this embodiment, the accepting vein may be located in one body location, such as the cephalic vein in an arm and the donating vein may be in another location, such as the femoral vein in a leg. In this instance, the two ends of the pump-conduit assembly will be located within the body and a bridging portion of the pump-conduit assembly may be extracorporeal (outside the body, e.g. worn under the clothing) or intracorporeal (inside the body, e.g. tunneled under the skin). Furthermore, in certain instances, the donating vessel may be more peripheral in relative body location than the accepting vein.

In another embodiment, a method comprises a surgical procedure that is performed to expose a segment of a peripheral artery and a segment of a peripheral vein. One end of a first synthetic conduit is fluidly connected to the peripheral artery. The other end of the first synthetic conduit is fluidly connected to the inflow port of a pump. One end of a second synthetic conduit is fluidly connected to the peripheral vein. The other end of the second synthetic conduit is fluidly connected to the outflow port of the same pump. Pumping oxygenated blood from the peripheral artery to the peripheral vein is performed until the vein has persistently dilated to the desired overall diameter and lumen diameter. Once the desired amount of vein enlargement has occurred, a second surgical procedure is performed to remove the pump and synthetic conduits. A hemodialysis access site (such as an AVF or AVG) or bypass graft can be created at this time, or a later time, using at least a portion of the persistently enlarged accepting vein. A variation of this embodiment is provided wherein the pump port may be fluidly connected directly to the artery or vein without using an interposed synthetic conduit.

In yet another embodiment, a pair of specialized catheters are inserted into the venous system. The first end of one catheter is attached to the inflow port of a pump (hereafter the "inflow catheter") while the first end of the other catheter is attached to the outflow port of the pump (hereafter the "outflow catheter"). Optionally, the two catheters can be joined together, such as with a double lumen catheter. The catheters are configured for insertion into the lumen of the venous system. After insertion, the tip of the second end of the inflow catheter is positioned in anywhere in the venous system where a sufficient amount of blood can be drawn into the inflow catheter (e.g. the right atrium, superior vena cava, subclavian vein, or brachiocephalic vein). After insertion, the tip of the second end of the outflow catheter is positioned in a segment of peripheral vein (the accepting vein) in the venous system where blood can be delivered by the outflow catheter (e.g. cephalic vein). The pump then draws deoxygenated blood into the lumen of the inflow catheter from the donating vein and discharges the blood from the outflow catheter and into the lumen of the accepting vein. In this embodiment, the pump and a portion of the inflow catheter and outflow catheters remain external to the patient. The pump is operated until the desired amount of persistent overall diameter and lumen diameter enlargement has occurred in the accepting vein, whereupon the pump and catheters are removed. A hemodialysis access site (such as an AVF or AVG) or bypass graft can be created at this time, or a later time, using at least a portion of the persistently enlarged accepting vein.

A system for increasing the blood speed and WSS in a vein by delivery of deoxygenated blood from a donating vein to an accepting vein in a patient is provided that comprises two synthetic conduits, each with two ends, a blood pump, a control unit, and a power source. This system may also contain one or more sensor units. In one embodiment of the system, the synthetic conduits and pump, collectively known as the "pump-conduit assembly" is configured to draw deoxygenated blood from the donating vein or the right atrium and pump that blood into the accepting vein. The pump-conduit assembly is configured to pump deoxygenated blood. In another embodiment of the system, the pump-conduit assembly is configured to draw oxygenated blood from a peripheral artery and pump the blood into a peripheral vein. The blood is pumped in a manner that increases the blood speed in the artery and vein and increases WSS exerted on the endothelium of the artery and vein for a period of time sufficient to cause a persistent increase in the overall diameter and lumen diameter of the peripheral artery and vein. Preferably, the blood being pumped into peripheral vein has low pulsatility, for example lower pulsatility than the blood in a peripheral artery. A variation of this embodiment is provided whereby the pump is fluidly connected directly to the artery or vein (or both) without using an interposed synthetic conduit. The pump includes an inlet and an outlet, and the pump is configured to deliver deoxygenated or oxygenated blood to the peripheral vein in a manner that increases the speed of the blood in the vein and the WSS exerted on the endothelium in the vein to cause a persistent increase in the overall diameter and the lumen diameter of the peripheral vein. The blood pump may be implanted in the patient, may remain external to the patient, or may have implanted and external portions. All or some of the synthetic conduits may be implanted in the patient, may be implanted subcutaneously, or may be implanted within the lumen of the venous system, or any combination thereof. The implanted portions of pump-conduit assembly may be monitored and adjusted periodically, for example, every seven days.

The invention includes methods of increasing the blood speed in a peripheral vein and increasing the WSS exerted on the endothelium of a peripheral vein of a human patient in need of a hemodialysis access site or a bypass graft are also provided. A device designed to augment arterial blood flow for the treatment of heart failure would be useful for this purpose. Specifically, a ventricular assist device (VAD) which is optimized for low blood flows would be capable of pumping blood from a donating vessel to a peripheral vein to induce a persistent increase in overall diameter and lumen diameter of the peripheral vein. In various embodiments, a pediatric VAD, or a miniature VAD designed to treat moderate heart failure in adults (such as the Synergy pump by Circulite) may be used. Other devices, including an LVAD or an RVAD that are optimized for low blood flows, may also be used.

The method comprises fluidly connecting the low-flow VAD, a derivative thereof, or a similar type device to a donating vessel, drawing blood from the donating vessel, and pumping it into the peripheral accepting vein for a sufficient amount of time to cause a desired amount of persistent increase in the overall diameter and the lumen diameter of the peripheral vein. The blood pump may be implanted into the patient or it may remain external to the patient. When the pump is external to the patient, it may be affixed to the patient for continuous pumping. Alternatively, the pump may be configured to detach from the donating and accepting vessels of the patient for periodic and/or intermittent pumping sessions.

The lumen diameter of peripheral accepting veins can be monitored while the blood is being pumped into the vein using conventional methods such as visualization with ultrasound or diagnostic angiography. A pump-conduit assembly or pump-catheter assembly may incorporate features that facilitate diagnostic angiography such as radiopaque markers that identify sites that can be accessed with needle for injection of contrast into the assembly that will subsequently flow into the accepting peripheral vein and make it visible during fluoroscopy using both conventional and digital subtraction angiography.

When a portion of a pump-conduit assembly or pump catheter assembly is located external to the body, then an antimicrobial coating or cuff may be affixed to the portion of the device that connects the implanted and external components. For example, when a controller and/or power source is strapped to the wrist, attached to a belt, or carried in a bag or pack, then the antimicrobial coating is placed on or around a connection and/or entry point where the device enters the patient's body.

These and other objects, features, aspects and advantages of the present invention will become apparent to those skilled in the art from the following detailed description, which, taken in conjunction with the annexed drawings, discloses preferred embodiments of the present invention.

BRIEF DESCRIPTION OF THE DRAWINGS

Referring now to the attached drawings which form a part of this original disclosure.

DETAILED DESCRIPTION OF THE PREFERRED EMBODIMENTS

Figure 1A:
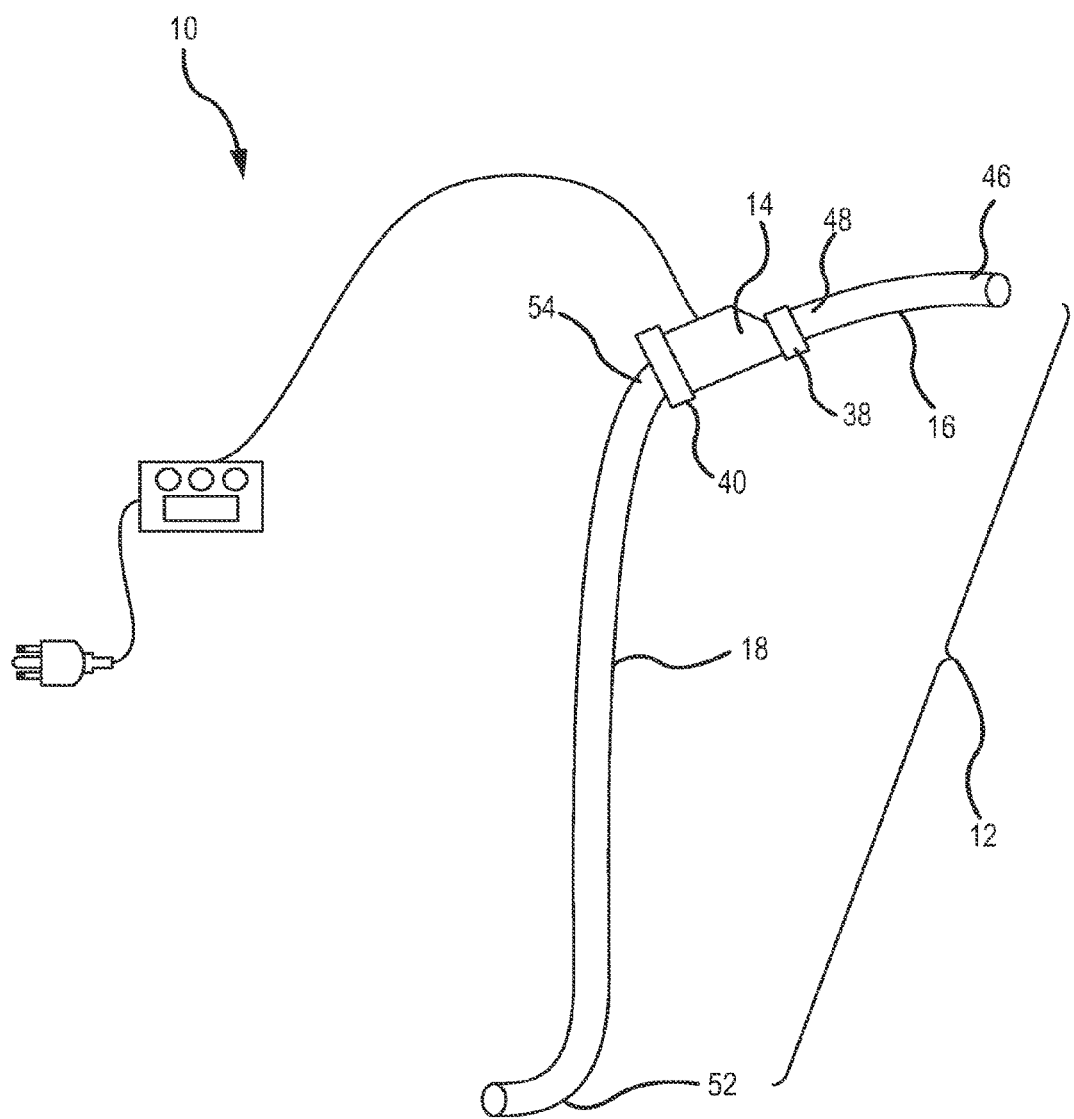
FIG. 1A is a schematic view of a pump-conduit assembly of a system and method in accordance with a first embodiment of the present invention.

Preferred embodiments of the present invention will now be explained with reference to the drawings. It will be apparent to those skilled in the art from this disclosure that the following description of the embodiments of the present invention is provided for illustration only and not for limiting the invention as defined by the appended claims and their equivalents. Referring initially to FIGS. 1-4, a system 10 to increase the overall diameter of veins is illustrated as used for a patient 20. The system 10 removes deoxygenated venous blood from the patient's venous system 22 and redirects that blood into the accepting peripheral vein 30. The system 10 also increases the speed of blood in the accepting peripheral vein 30 and increases the WSS exerted on the endothelium of the accepting peripheral vein 30, to increase the diameter of the accepting peripheral vein 30 located, for example, in an arm 24 or a leg 26. The diameter of blood vessels such as peripheral veins can be determined by measuring the diameter of the lumen, which is the open space at the center of blood vessel where blood is flowing. For the purpose of this application, this measurement is referred to as "lumen diameter". The diameter of blood vessels can be determined by measuring the diameter in a manner that includes the wall of the blood vessel. For the purpose of this application, this measurement is referred to as "overall diameter". The invention relates to simultaneously and persistently increasing the overall diameter and lumen diameter of a peripheral vein by directing blood (preferably with low pulsatility) into the peripheral vein, thereby increasing the speed of the blood in the peripheral vein and increasing the WSS on the endothelium of the peripheral vein. Systems and methods are described wherein the speed of the blood in a peripheral vein and the WSS on the endothelium of the peripheral vein is increased by using a pump. Preferably, the pump directs blood into the peripheral vein, wherein the pumped blood has reduced pulsatility, such as when the pulse pressure is lower than blood in a peripheral artery.

The systems and methods described herein increase the WSS level in a peripheral vein. Normal WSS for veins ranges between 0.076 Pa and 0.76 Pa. The systems and methods described herein are configured to increase the WSS level in the accepting peripheral vein to range from about 0.76 Pa and 23 Pa, preferably to a range between 2.5 Pa and 7.5 Pa. Sustained WSS less than 0.76 Pa might dilate veins but at a rate that is comparatively slow. Sustained WSS greater than 23 Pa are likely to cause denudation (loss) of the endothelium of the vein, which is known to retard dilation of blood vessels in response to increases in blood speed and WSS. Pumping blood in a manner that increases WSS to the desired range for preferably at least 7 days, and more preferably between about 14 and 84 days, for example, produces an amount of persistent dilation in the accepting peripheral vein such that veins that were initially ineligible for use as a hemodialysis access site or bypass graft due to small vein diameter become usable. The blood pumping process may be monitored and adjusted periodically. For example, the pump may be adjusted every seven days to account for changes in the peripheral vein prior to achieving the desired persistent dilation.

The systems and methods described herein also increase the speed of blood in peripheral veins and in certain instances, peripheral arteries. At rest, the mean speed of blood in the cephalic vein in humans is generally between 5-9 cm/s, while the speed of blood in the brachial artery is generally between 10-15 cm/s. For the systems and methods described herein, the mean speed of blood in the peripheral vein is increased to a range between 15 cm/s-100 cm/s, preferably to a range between 25 cm/s and 100 cm/s, depending on the diameter of peripheral accepting vein and the length of time the pumping of blood into the peripheral accepting vein is planned. Preferably, the mean blood speed is increased for between 7 days and 84 days, or preferably between 7 and 42 days, to induce persistent dilation in the peripheral accepting vein such that veins that were initially ineligible for use as a hemodialysis access site or bypass graft due to a small vein diameter become usable. This can also be accomplished by intermittently increasing mean blood speed during the treatment period, with intervening periods of normal mean blood speed.

Studies have shown hemodynamic forces and changes in hemodynamic forces within veins play a vital role in determining the overall diameter and lumen diameter of those veins. For example, persistent increases in blood speed and WSS can lead to vein dilation. The elevated blood speed and WSS are sensed by endothelial cells, which trigger signaling mechanisms that result in stimulation of vascular smooth muscle cells, attraction of monocytes and macrophages, and synthesis and release of proteases capable of degrading components of the extracellular matrix such as collagen and elastin. As such, the present invention relates to increasing blood speed and WSS for a period of time sufficient to result in vein remodeling and dilation.

Assuming a Hagen-Poiseuille blood flow in the vessel (i.e. a laminar flow with a fully developed parabolic velocity profile), then WSS can be determined using the equation:

$$WSS(\tau) = 4Q\lambda/\pi R^3, \text{ where:}$$

Q=volume flow rate in mL/s
μ=viscosity of blood in units of poise
R=radius of vessel in cm
τ=wall shear stress in dynes/cm$^2$ The systems and methods described herein increase the WSS level in a peripheral vein. Normal WSS for veins ranges between 0.076 Pa and 0.76 Pa. The systems and methods described herein increase the WSS level to a range between 0.76 Pa and 23 Pa, preferably to a range between 2.5 Pa and 7.5 Pa. Preferably, the WSS is increased for between 7 days and 84 days, or preferably between 7 and 42 days, to induce persistent dilation in the peripheral accepting vein such that veins that were initially ineligible for use as a hemodialysis access site or bypass graft due to a small vein diameter become usable. This can also be accomplished by intermittently increasing WSS during the treatment period, with intervening periods of normal WSS.

WSS levels in the accepting peripheral vein lower than 0.076 Pa may dilate veins however, this would likely occurs at a slow rate. WSS levels in accepting peripheral veins higher than about 23 Pa are likely to cause denudation (loss) of the endothelium of the veins. Denudation of the endothelium of blood vessels is known to retard dilation in the setting of increased in blood speed and WSS. The increased WSS induces sufficient persistent dilation in the veins, such that those that were initially ineligible for use as a hemodialysis access site or bypass graft due to a small diameter become usable. The diameter of the accepting vein can be determined intermittently, such as every 7-14 days for example, to allow for pump speed adjustment in order to optimize vein dilation during the treatment period.

The systems and methods described herein also increase the speed of blood in peripheral veins and in certain instances, peripheral arteries. At rest, the mean speed of blood in the cephalic vein in humans is generally between 5-9 cm/s, while the speed of blood in the brachial artery is generally between 10-15 cm/s. For the systems and methods described herein, the mean speed of blood in the peripheral vein is increased to a range between 15 cm/s-100 cm/s, preferably to a range between 25 cm/s and 100 cm/s, depending on the diameter of peripheral accepting vein and the length of time the pumping of blood into the peripheral accepting vein is planned. Preferably, the mean blood speed is increased for between 7 days and 84 days, or preferably between 7 and 42 days, to induce persistent dilation in the peripheral accepting vein such that veins that were initially ineligible for use as a hemodialysis access site or bypass graft due to a small vein diameter become usable. Mean blood speed levels in the accepting peripheral vein lower than 15 cm/s may dilate veins however, this would likely occurs at a slow rate. Mean blood velocity levels in accepting peripheral veins higher than about 100 cm/s are likely to cause denudation (loss) of the endothelium of the veins. Denudation of the endothelium of blood vessels is known to retard dilation in the setting of increased in blood speed. The increased mean blood speed induces sufficient persistent dilation in the veins, such that those that were initially ineligible for use as a hemodialysis access site or bypass graft due to a small diameter become usable. The diameter of the accepting vein can be determined intermittently, such as every 7-14 days for example, to allow for pump speed adjustment in order to optimize vein dilation during the treatment period.

Figure 2A:
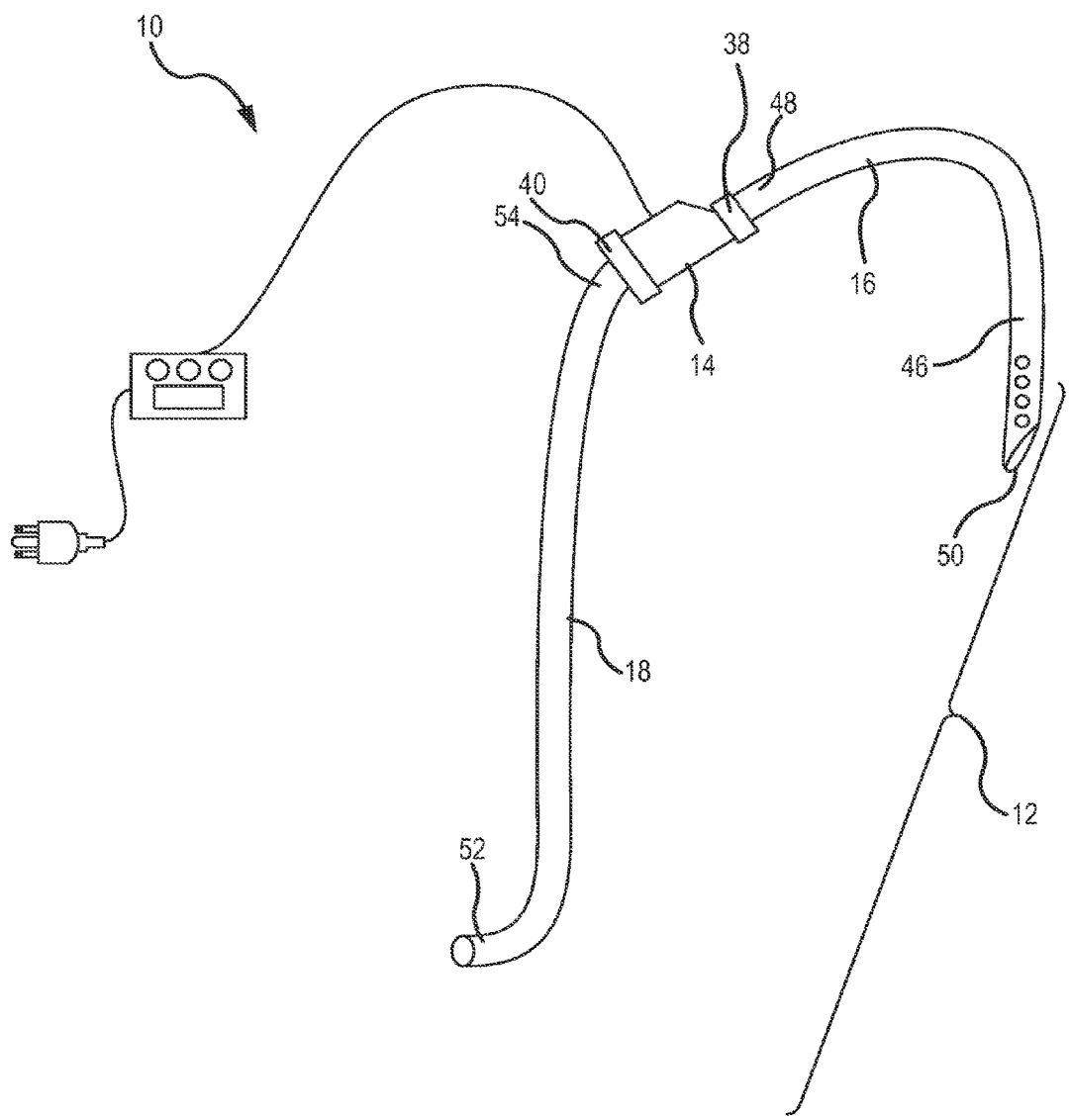
FIG. 2A is a schematic view of a pump-conduit assembly of a system and method in accordance with a second embodiment of the present invention.
Figure 2B:
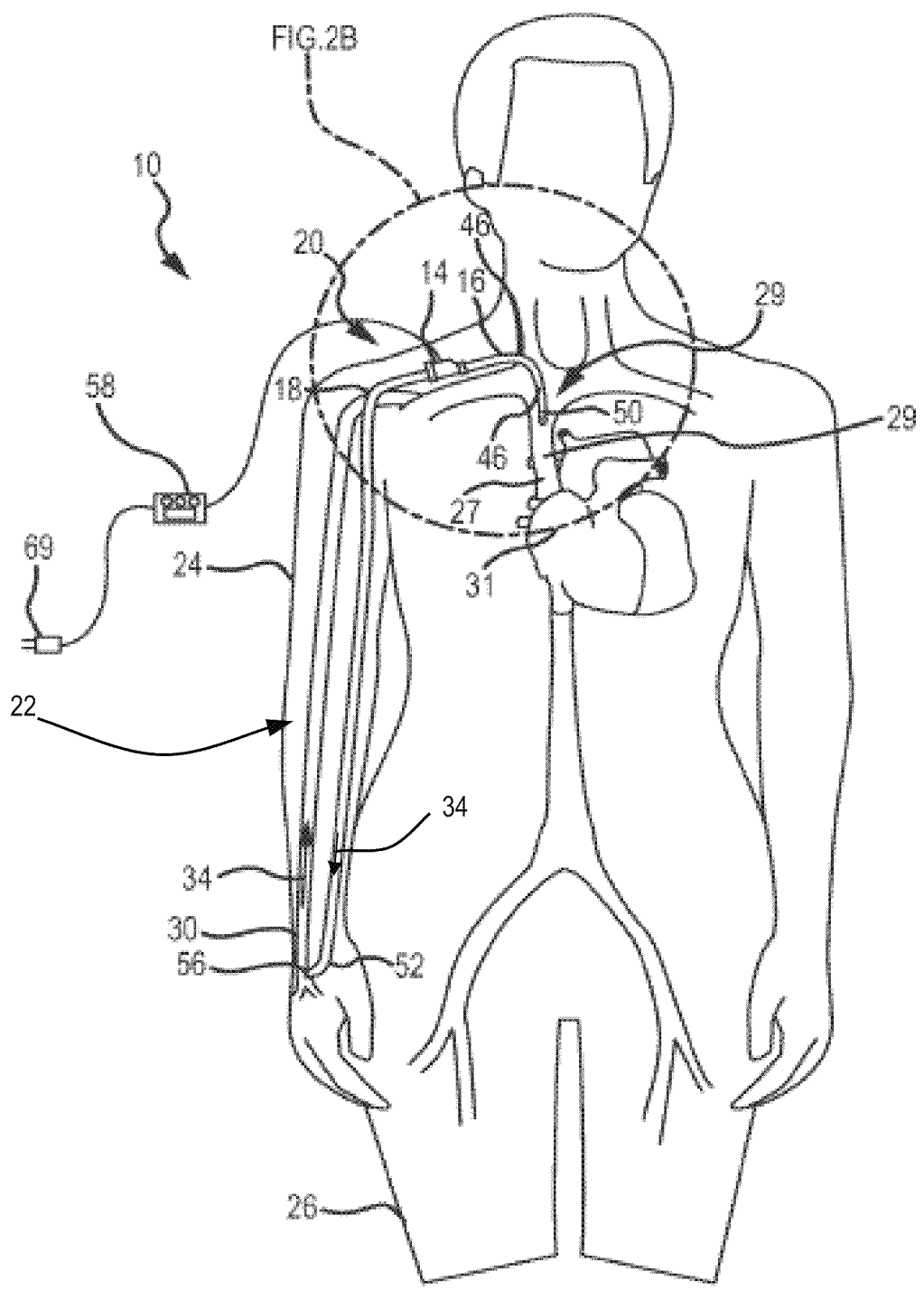
FIG. 2B is a schematic view of the pump-conduit assembly of FIG. 2A as applied to a circulatory system of a patient in accordance with the second embodiment of the present invention.
Figure 2C:
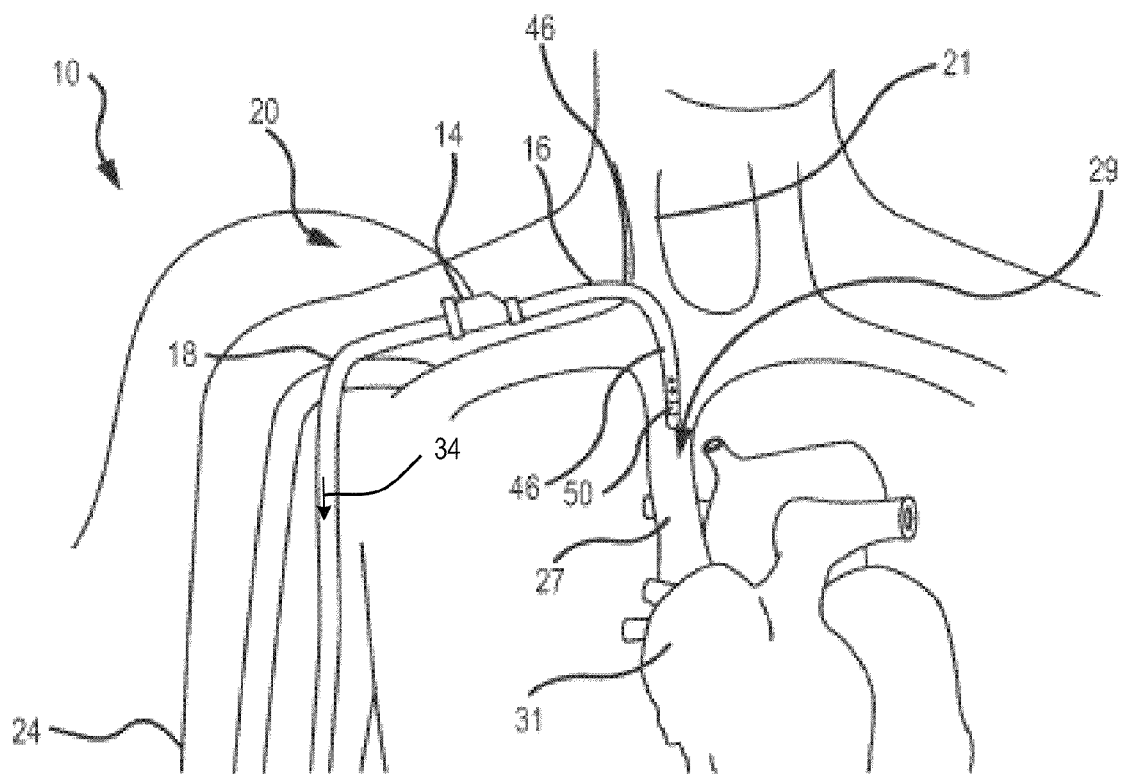
FIG. 2C is a magnified view of a portion of FIG. 2B.
Figure 3:
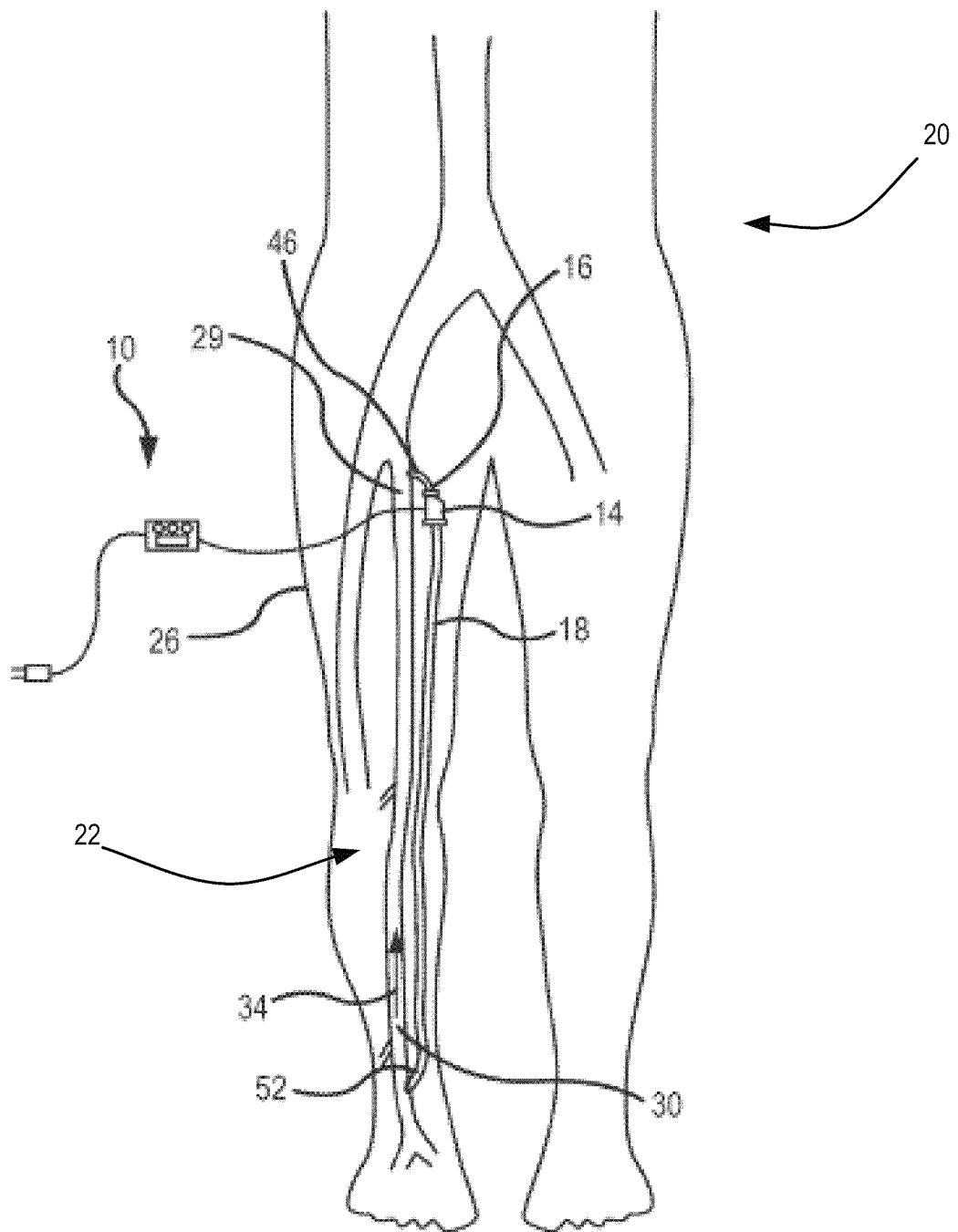
FIG. 3 is a schematic view of a pump-conduit assembly of a system and method as applied to a circulatory system of a patient in accordance with a third embodiment of the present invention.

Referring to FIGS. 1-3, the system 10 includes a pump-conduit assembly 12 for directing deoxygenated venous blood from a donating vein 29 of the venous system 22 of the patient 20 to the peripheral or accepting vein 30. In various embodiments, the peripheral or accepting vein 30 may be a cephalic vein, radial vein, median vein, ulnar vein, antecubital vein, median cephalic vein, median basilic vein, basilic vein, brachial vein, lesser saphenous vein, greater saphenous vein, or femoral vein. Other veins that might be useful in the creation of a hemodialysis access site or bypass graft or other veins useful for other vascular surgery procedures requiring the use of veins may be used. The pump-conduit assembly 12 delivers the deoxygenated blood to the peripheral or accepting vein 30. The rapid speed of the blood 34 and the elevated WSS in the peripheral vein 30 causes the peripheral or accepting vein 30 to enlarge over time. Thus, the system 10 and method 100 (referring to FIGS. 7-9) of the present invention advantageously increases the diameter of the peripheral or accepting vein 30 so that it can be used, for example, to construct an AVF or AVG access site for hemodialysis or as a bypass graft.

As used herein, deoxygenated blood is blood that has passed through the capillary system and had oxygen removed by the surrounding tissues and then passed into the venous system 22. A peripheral vein 30, as used herein, means any vein with a portion residing outside of the chest, abdomen, or pelvis. In the embodiment shown in FIGS. 1A and 2A, the peripheral or accepting vein 30 is the cephalic vein. However, in other embodiments, the peripheral vein 30 may be a radial vein, median vein, ulnar vein, antecubital vein, median cephalic vein, median basilic vein, basilic vein, brachial vein, lesser saphenous vein, greater saphenous vein, or femoral vein. In addition to a peripheral vein, other veins that might be useful in the creation of a hemodialysis access site or bypass graft or other veins useful for other vascular surgery procedures requiring the use of veins may also be used, such as those residing in the chest, abdomen, and pelvis.

In order to reduce pulsatility and/or provided low-pulsatile flow, a number of pulsatility dampening techniques may be used. By way of example, and not limitation, such techniques include tuning the head-flow characteristics of a blood pump, adding compliance to the pump outflow, and/or modulating the pump speed.

An AVF created using the cephalic vein at the wrist is a preferred form of vascular access for hemodialysis but this vein is frequently of inadequate diameter to facilitate the creation of an AVF in this location. Thus, the present invention is most advantageous to creating wrist AVFs in ESRD patients and increasing the percentage of ESRD patients that receive hemodialysis using a wrist AVF as a vascular access site.

Figure 6:
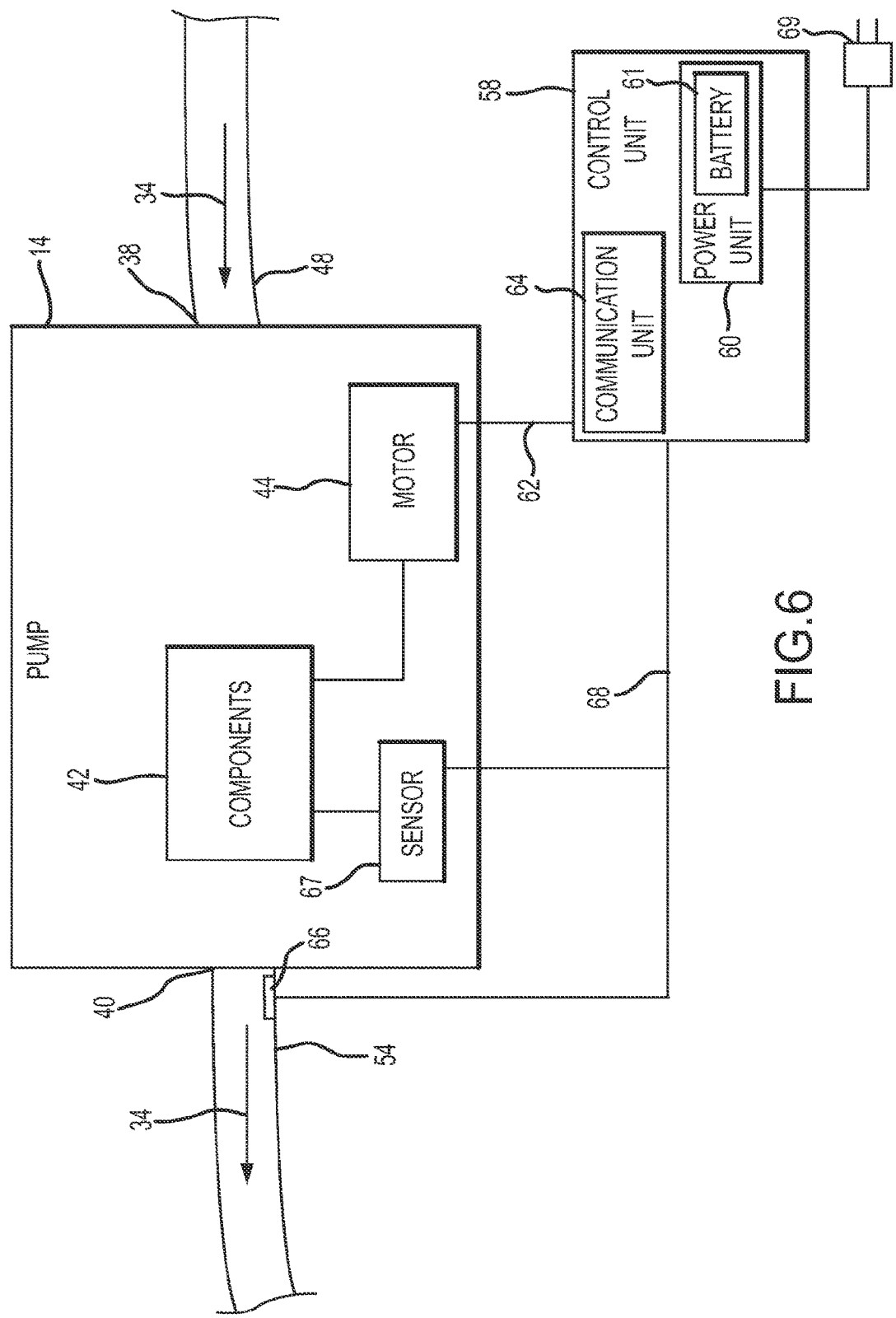
FIG. 6 is a schematic diagram of a pump operated in conjunction with a control unit for use in any of the above-mentioned embodiments.

The pump-conduit assembly 12 includes a blood pump 14 and synthetic conduits 16 and 18, i.e. an inflow conduit 16 and an outflow conduit 18. Blood pumps have been developed as a component of ventricular assist devices (VADs) and have been miniaturized to treat both adult patients with moderate heart failure and pediatric patients. These pumps can be implanted or remain external to the patient and are usually connected to a controller and a power source. Referring to FIG. 6, a schematic diagram of the pump-conduit assembly 12 is illustrated. The pump 14 can be a rotary pump such as an axial, mixed flow, or centrifugal pump. Without recognizing specific limitations, the bearing for the pump 14 can be constructed with magnetic fields, with hydrodynamic forces, or using a mechanical contact bearing such as a double-pin bearing. Pumps used in pediatric VAD systems or other low flow VAD systems can be used. Alternatively, the pump 14 can be an extracardiac pump such as that shown and described in U.S. Pat. Nos. 6,015,272 and 6,244,835, both of which are hereby incorporated herein by reference. These pumps are suitable for use in the system 10 and method 100 of the present invention. The pump 14 has an inlet 38 to receive deoxygenated blood drawn through the inflow conduit 16 and an outlet 40 for blood flow 34 to exit the pump 14. In regards to pumps used in pediatric VAD systems or other low flow VAD systems suitable for use as pump 14 of the present invention, these pumps can be sized as small as about the size of a AA battery or the diameter of a United States half dollar or quarter, and can weigh as little as about 25-35 g or less. These pumps are designed to pump about 0.3 to 1.5 L/min or 1 to 2.5 L/min, for example. Modifications to these pumps could be made to reduce this range to as low as 0.05 L/min for use in small diameter veins. A priming volume can be about 0.5-0.6 ml, for example. The blood-contacting surfaces of the pump 14 preferably include $Ti_6Al_4V$ and commercially pure titanium alloys and can include other materials such as injection-moldable ceramics and polymers, and alternative titanium alloys, e.g. $Ti_6Al_7Nb$. The blood-contacting surface also preferably has one or more coatings and surface treatments. As such, any of a variety of pumping devices can be used so long as it can be connected to the vascular system and can pump a sufficient amount of blood such that the desired WSS is achieved in the accepting vein.

The pump 14 includes various components 42 and a motor 44, as shown in FIG. 6. The various components 42 and motor 44 can be those common to a VAD. For example, the components 42 include one or more of a shaft, impeller blades, bearings, stator vanes, rotor, or stator. The rotor can be magnetically levitated. The motor 44 can include a stator, rotor, coil, and magnets. The motor 44 may be any suitable electric motor, such as a multi-phase motor controlled via pulse-width modulated current.

The system 10 and method 100 can utilize one or more of the pumps described in the following publications: The PediaFlow™ Pediatric Ventricular Assist Device, P. Wearden, et al., Pediatric Cardiac Surgery Annual, pp. 92-98, 2006; J. Wu et al., Designing with Heart, ANSYS Advantage, Vol. 1, Iss. 2, pp. s12-s13, 2007; and J. Baldwin, et al., The National Heart, Lung, and Blood Institute Pediatric Circulatory Support Program, Circulation, Vol. 113, pp. 147-155, 2006. Other examples of pumps that can be used as the pump 14 include: the Novacor, PediaFlow, Levacor, or MiVAD from World Heart, Inc.; the Debakey Heart Assist 1-5 from Micromed, Inc.; the HeartMate XVE, HeartMate II, HeartMate III, IVAD, or PVAD from Thoratec, Inc.; the Impella, BVS5000, AB5000, or Symphony from Abiomed, Inc.; the Tandem-Heart from CardiacAssist, Inc.; the VentrAssist from Ventracor, Inc.; the Incor or Excor from Berlin Heart, GmbH; the Duraheart from Terumo, Inc.; the HVAD or MVAD from HeartWare, Inc.; the Jarvik 2000 Flowmaker or Pediatric Jarvik 2000 Flowmaker from Jarvik Heart, Inc.; the Gyro C1E3 from Kyocera, Inc.; the CorAide or PediPump from the Cleveland Clinic Foundation; the MEDOS HIA VAD from MEDOS Medizintechnik AG; the pCAS from Ension, Inc; the Synergy from Circulite, Inc; the CentriMag, PediMag, and UltraMag from Levitronix, LLC; and, the BP-50 and BP-80 from Medtronic, Inc. The pumps can be monitored and adjusted manually or with a software program, application, or other automated system. The software program can automatically adjust the pump speed to maintain the desired amount of blood flow and WSS in the accepting vein. Alternatively, the vein diameter and blood flow may be periodically checked manually and the pump may be manually adjusted, for example, by tuning the head-flow characteristics of the pump, adding compliance to the pump outflow, and/or modulating the pump speed. Other adjustments may also be made.

The synthetic conduits 16 and 18 are comprised of PTFE and/or Dacron, preferentially reinforced so that the synthetic conduits 16 and 18 are less susceptible to kinking and obstruction. All or a portion of the conduits 16 and 18 may be comprised of materials commonly used to make hemodialysis catheters such as polyvinyl chloride, polyethylene, polyurethane, and/or silicone. The synthetic conduits 16 and 18 can be of any material or combination of materials so long as the conduits 16 and 18 exhibit necessary characteristics, such as flexibility, sterility, resistance to kinking, and can be connected to a blood vessel via an anastomosis or inserted into the lumen of a blood vessel, as needed. In addition, the synthetic conduits 16 and 18 preferably exhibit the characteristics needed for tunneling (as necessary) and have luminal surfaces that are resistant to thrombosis. As another example, the synthetic conduits 16 and 18 can have an exterior layer composed of a different material than the luminal layer. The synthetic conduits 16 and 18 can also be coated with silicon to aid in removal from the body and avoid latex allergies. In certain embodiments, the connection between the synthetic conduit 16 or 18 and the vein 29 or 30 is made using a conventional surgical anastomosis, using suture in a running or divided fashion, henceforth described as an "anastomotic connection." An anastomotic connection can also be made with surgical clips and other standard ways of making an anastomosis.

Figure 1B:
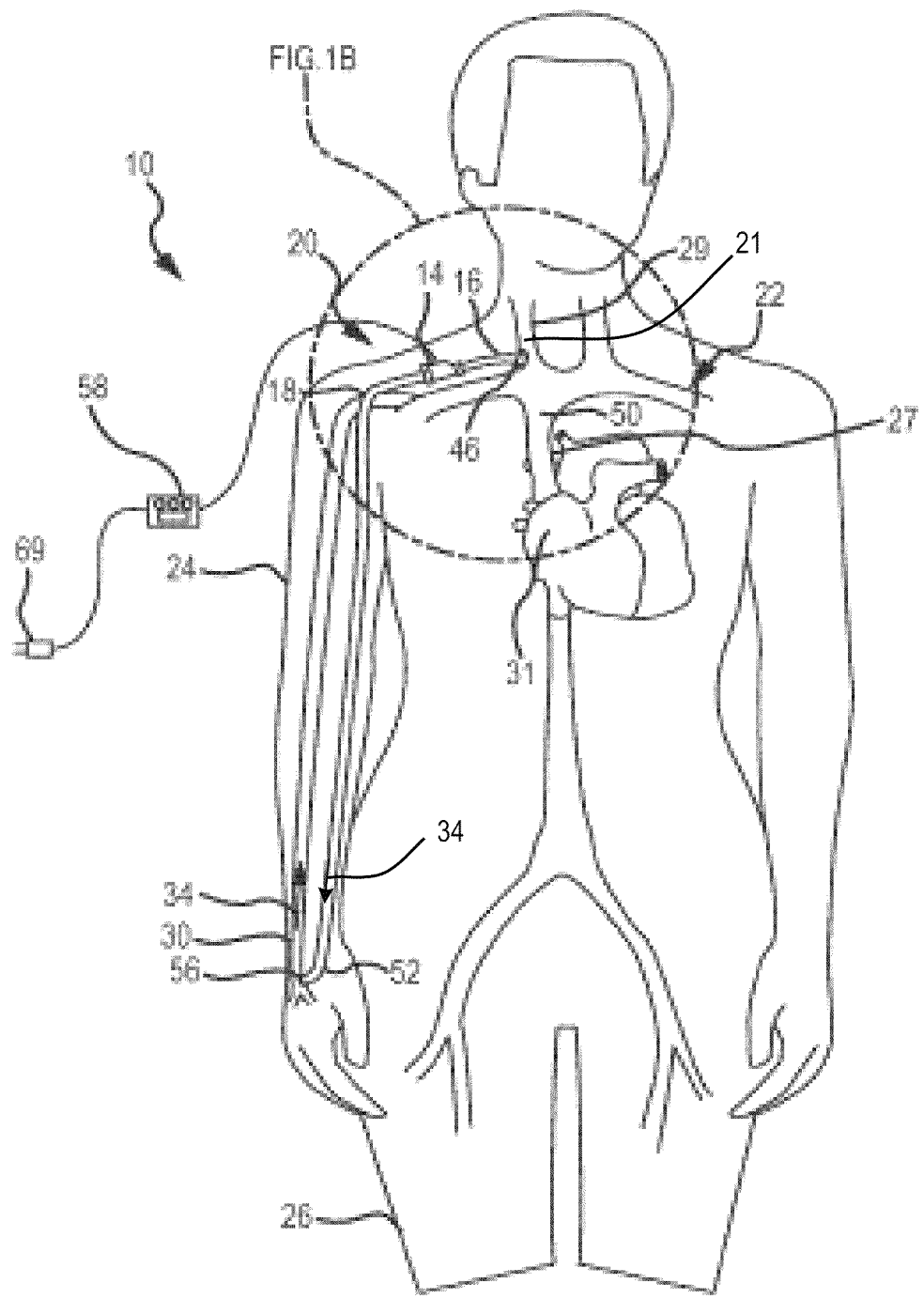
FIG. 1B is a schematic view of the pump-conduit assembly of FIG. 1A as applied to a circulatory system of a patient in accordance with the first embodiment of the present invention.
Figure 1C:
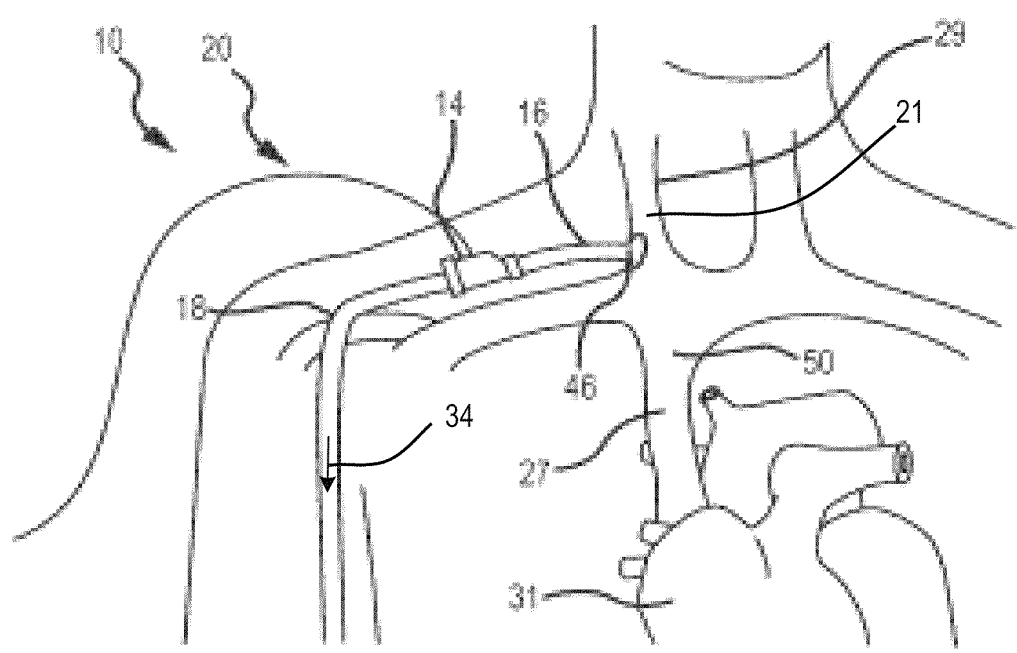
FIG. 1C is a magnified view of a portion of FIG. 1B.

Referring to FIGS. 1-3, the synthetic inflow conduit 16 has a first end 46 configured to fluidly connect to a donating vein 29 or the right atrium 31 of the heart and a second end 48 connected to the inlet 38 of the pump 14. The donating vein 29 can include an antecubital vein, basilic vein, brachial vein, axillary vein, subclavian vein, jugular vein, brachiocephalic vein, superior vena cava, lesser saphenous vein, greater saphenous vein, femoral vein, common iliac vein, external iliac vein, superior vena cava, inferior vena cava, or other veins capable of providing sufficient blood flow to the pump for the purpose of causing persistent dilation of the accepting peripheral vein. The synthetic outflow conduit 18 has a first end 52 configured to fluidly connect to the peripheral accepting vein 30 and a second end 54 connected to the outlet 40 of the pump 14. The pump-conduit assembly 12 is configured to redirect blood from the donating vein 29 to the peripheral accepting vein 30 in a manner that increases the blood speed and WSS in the peripheral vein to the desired level for a period of time sufficient to cause a persistent increase in the overall diameter and lumen diameter of the peripheral vein. In certain embodiments, a portion of the synthetic conduits 16, 18 may be extracorporeal to the patient 20. Referring to FIGS. 1 and 3, the first end 46 of the inflow conduit 16 and the first end 52 of the outflow conduit 18 are configured for an anastomotic connection. As shown in FIGS. 1B and 1C, the first end 46 is fluidly connected to the internal jugular vein (which serves as the donating vein 29) via an anastomotic connection and the first end 52 of the outflow conduit 18 is fluidly connected to the cephalic vein (which serves as the peripheral accepting vein 30) via an anastomotic connection.

Referring to FIGS. 2A-2C, the first end 46 of the synthetic inflow conduit 16 is configured as a catheter. The fluid connection between the synthetic inflow conduit 16 and the venous system is made by positioning the tip of the catheter portion 50 of the synthetic inflow conduit into the superior vena cava 27, henceforth described as a "catheter connection". When a catheter connection is made with a donating vein 29 (in this case, the superior vena cava 27), the catheter portion 50 of the synthetic inflow conduit 46 may enter the venous system at any location where the vein lumen diameter is adequate to accept the catheter portion 50. The tip of the catheter portion 50 may be placed at any location where sufficient blood can be drawn into the catheter to provide the desired blood flow 34 to the accepting vein 30. Preferred locations for the tip of the catheter portion 50 include, but are not limited to a brachiocephalic vein, the superior vena cava 27, and the right atrium 31. In the embodiment illustrated in FIGS. 2B-2C, the system 10 draws deoxygenated blood from the superior vena cava 27 of the patient 20 and redirects it to the cephalic vein 30 in the arm 24.

In another embodiment shown in FIG. 3, the system 10 redirects deoxygenated venous blood from donating vein 29 (in this case, the more central portion of the greater saphenous vein) to the peripheral accepting vein 30 (in this case, a more peripheral portion of the greater saphenous vein) in the leg 26 thereby increasing the speed of blood and WSS in the accepting vein to the desired level and for a period of time sufficient to cause a persistent increase in the lumen diameter and overall diameter of the accepting greater saphenous vein 30. In the embodiment shown in FIG. 3, the inflow conduit 16 is fluidly connected to a greater saphenous vein 29 of the patient 20 via an anastomotic connection. In some embodiments, the blood is pumped into the accepting vein with a pulsatility that is reduced when compared with the pulsatility of blood in a peripheral artery. For example, the mean pulse pressure in the accepting vein adjacent to the connection with the outflow conduit is <40 mmHg, <30 mmHg, <20 mmHg, <10 mmHg, or preferably <5 mmHg with the pump operating. The pumping of blood into the peripheral vein and the increase in blood speed and WSS continues for a period of time sufficient to cause a persistent increase in the overall diameter and lumen diameter of the accepting greater saphenous vein segment 30 to facilitate extraction and autotransplantation as part of a surgery to create a cardiac or peripheral bypass graft, or other surgery that requires autotransplantation of a portion of a patient's vein.

Figure 4A:
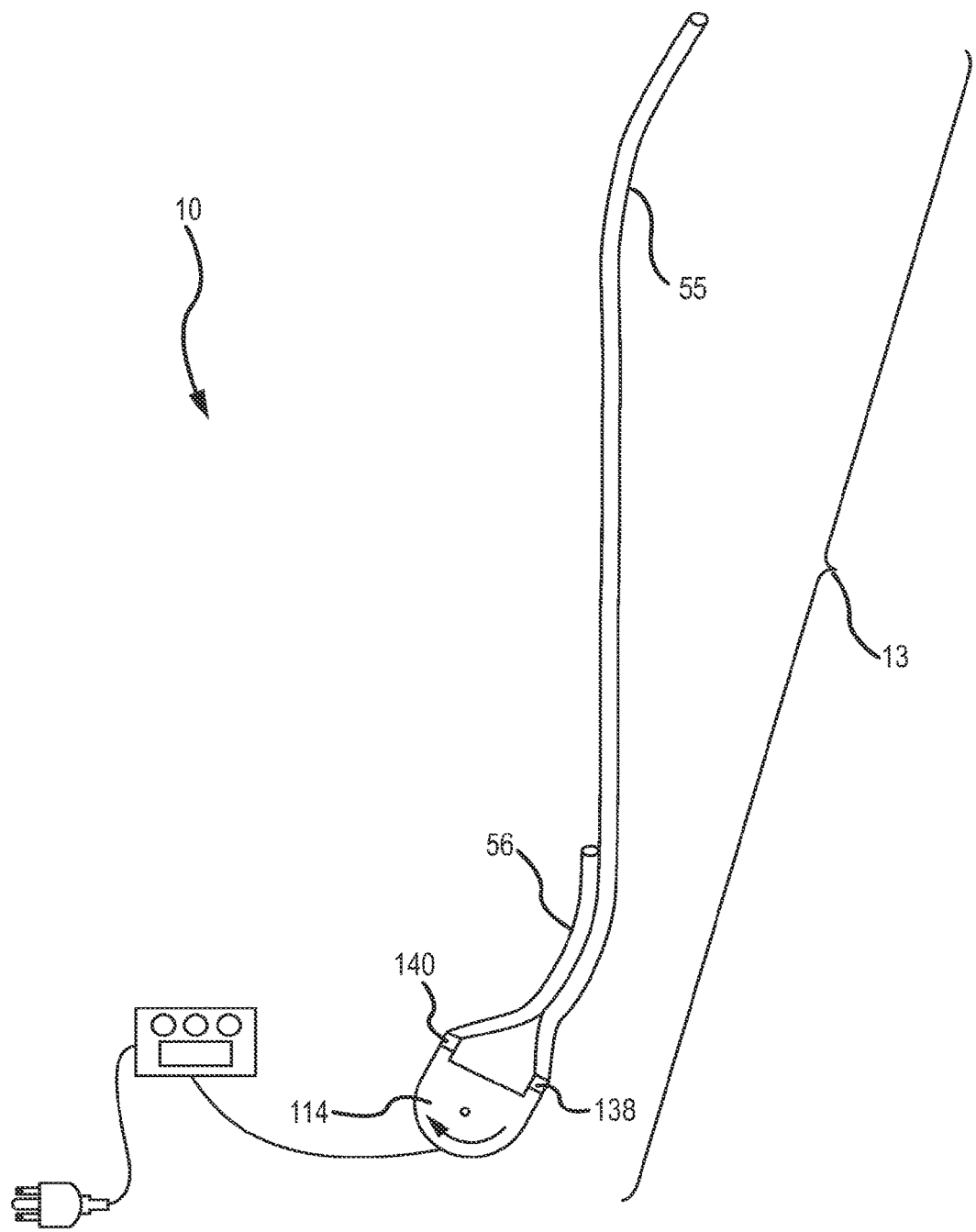
FIG. 4A is a schematic view of a pump-catheter assembly of a system and method in accordance with a fourth embodiment of the present invention.

Referring to FIG. 4A, in another embodiment, an extracorporeal pump 114 is attached to two specialized catheters, an inflow catheter 55, and an outflow catheter 56 to form a catheter-pump assembly 13. The pump 114 draws deoxygenated blood into the lumen of the inflow catheter 55 from the donating vein 29 and then discharges the blood from the outflow catheter 56 and into the lumen of the peripheral accepting vein 30, thereby increasing the speed of blood and the WSS in the peripheral accepting vein 30.

Figure 4B:
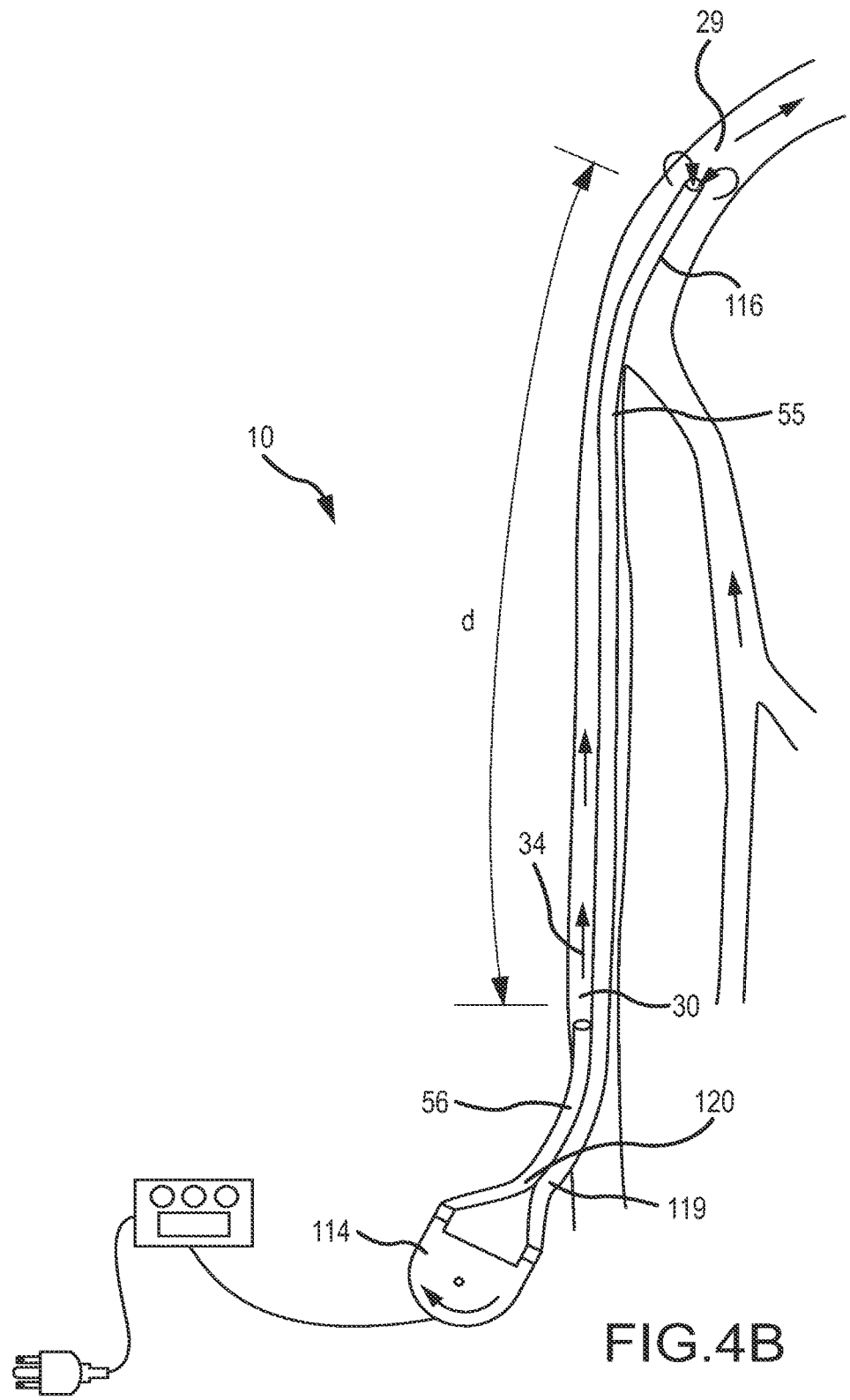
FIG. 4B is a schematic view of the pump-catheter assembly of FIG. 4A as applied to a circulatory system of a patient in accordance with the fourth embodiment of the present invention.

FIGS. 4A and 4B illustrate another embodiment of the system 10. The pump-catheter assembly 13 is configured to increase the blood speed and WSS in vein segment d. The inflow catheter 55 and the outflow catheter 56 may optionally be joined in all or some portions (such as with a double lumen catheter) and can be percutaneously inserted into the lumen of the accepting peripheral vein 30, obviating the need for an invasive surgical procedure. For this embodiment, a portion of the catheter can be tunneled subcutaneously before exiting the skin in order to reduce the risk of infection. Extracorporeal portions of the catheters 119 and 120 and the extracorporeal pump 114 can be affixed to the body, connected to a power source, and operated in a manner that increases the speed of the blood 34 and WSS in segment d of the accepting peripheral vein 30 for a period of time sufficient to cause a persistent increase the overall diameter and lumen diameter of segment d of the accepting peripheral vein 30. Once the desired amount of diameter enlargement has occurred in segment d of the accepting peripheral vein 30, the pump-catheter assembly 12 is removed and a surgical procedure can be performed to create a hemodialysis access site or bypass graft using at least a portion of the enlarged segment d of the accepting peripheral vein 30, either at the same time or in a subsequent operation.

Figure 5A:
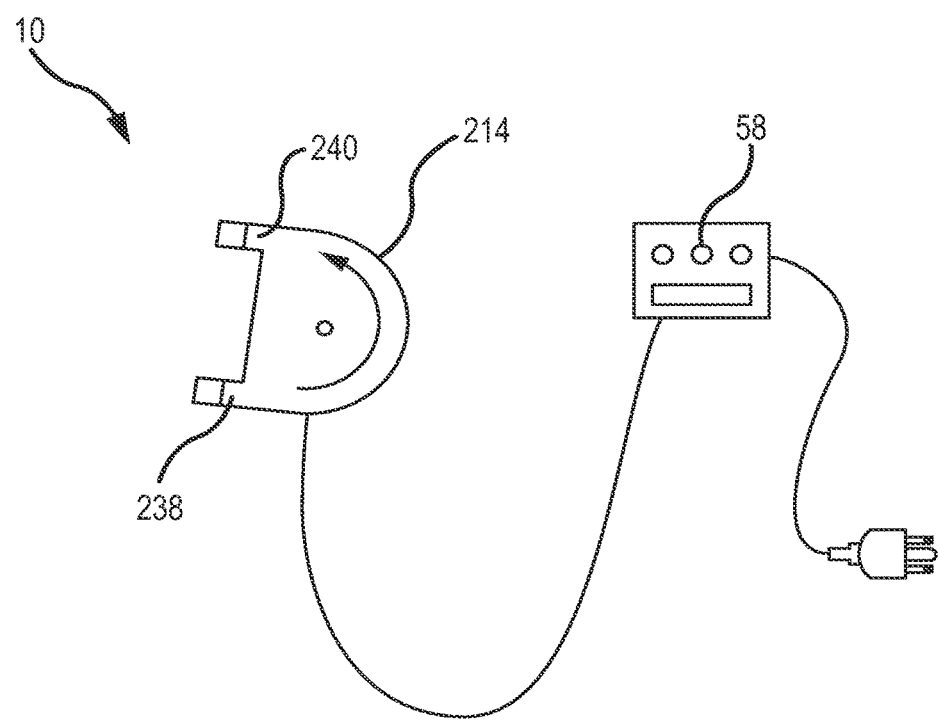
FIG. 5A is a schematic view of a pump-conduit assembly of a system and method in accordance with a fifth embodiment of the present invention.
Figure 5B:
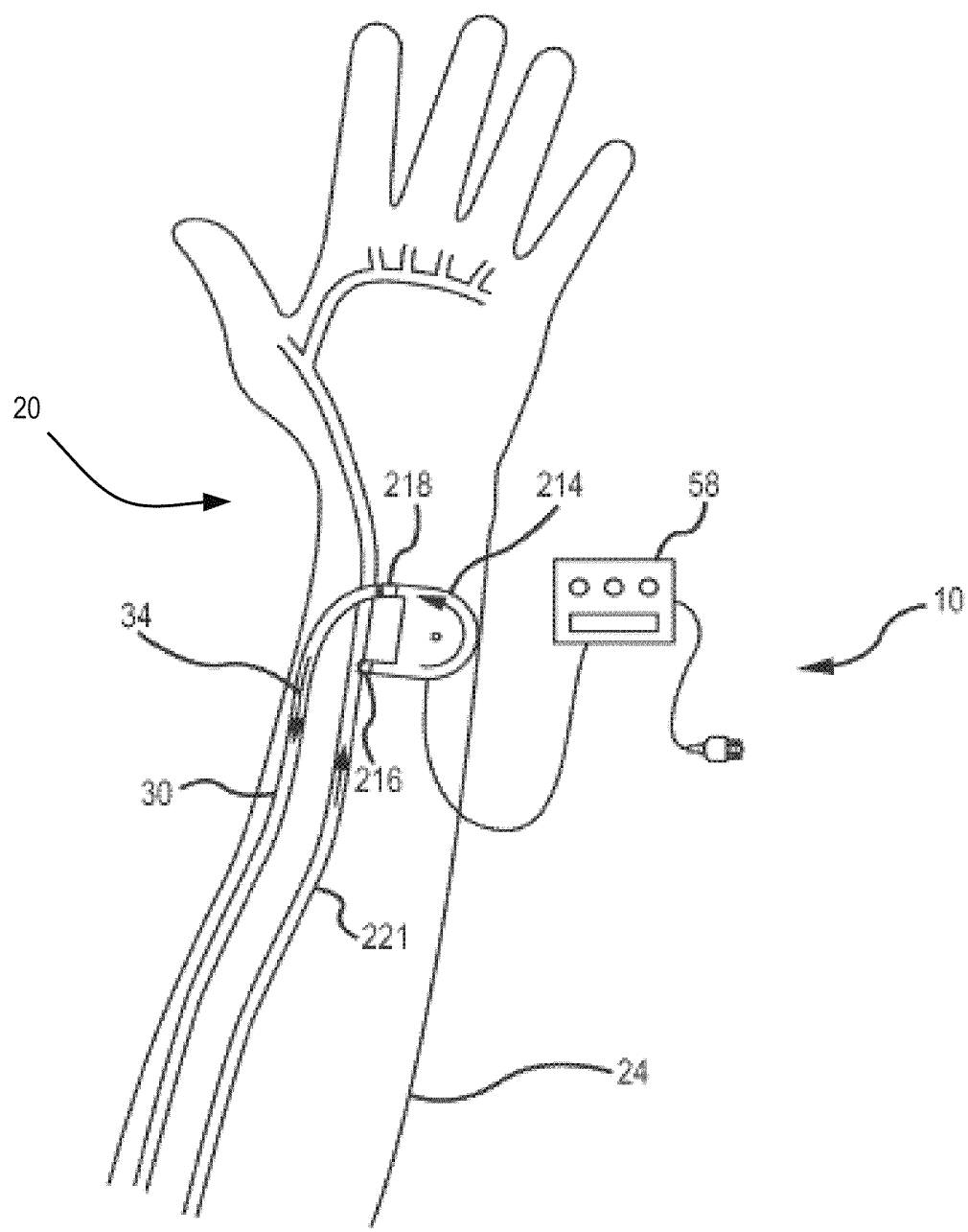
FIG. 5B is a schematic view of the pump-conduit assembly of FIG. 5A as applied to a circulatory system of a patient in accordance with the fifth embodiment of the present invention.

Referring to FIGS. 5A and 5B, a system 10 to increase the overall diameter of veins is illustrated as used for a patient 20. The system 10 removes oxygenated arterial blood from a patient's peripheral artery 221 and redirects that blood into the accepting peripheral vein 30 and is configured and operated to increase the blood speed and WSS in the accepting peripheral vein 30 for a period of time sufficient to cause a persistent increase in the diameter of the accepting peripheral vein 30 in, for example, an arm 24 or a leg 26. An embodiment of a system 10 in which a pump 214 is implanted in the arm 24 is illustrated. The pump 214 has an inlet 216 connected to an artery 221 in the arm 24 via anastomotic connection. The pump 214 also has an outlet 218 connected to the peripheral vein 30 via an anastomotic connection. The pump 214 is controlled and powered by the control unit 58. In operation, the pump 214 withdraws blood from the artery 221 and pumps the blood into the peripheral vein 30. This embodiment can allow the performance of a surgical procedure that avoids the need for extended synthetic conduits and increases blood speed and WSS in both the peripheral vein 30 and the peripheral artery 221 resulting in, if operated for a sufficient period of time, simultaneous dilation of the vein 30 and the artery 221. Specifically, the pump 214 is implanted in the forearm of the patient 20. Once the desired amount of diameter enlargement has occurred in the accepting peripheral vein 30, the pump 214 can be removed and a surgical procedure can be performed to create a hemodialysis access site or bypass graft using at least a portion the enlarged artery 221 or vein 30, either at that time or during a subsequent operation.

In various embodiments, oxygenated arterial blood may be drawn from a donating artery. Donating arteries may include, but are not limited to, a radial artery, ulnar artery, interosseous artery, brachial artery, anterior tibial artery, posterior tibial artery, peroneal artery, popliteal artery, profunda artery, superficial femoral artery, or femoral artery.

Referring to FIG. 6, a schematic of an embodiment of the system 10 is illustrated. The control unit 58 is connected to the pump 14 and is configured to control the speed of the pump 14 and collect information on the function of the pump 14. The control unit 58 may be implanted in the patient 20, may remain external to the patient 20, or may have implanted and external portions. A power source is embodied in a power unit 60 and is connected to the control unit 58 and the pump 14. The power unit 60 provides energy to the pump 14 and the control unit 58 for routine operation. The power unit 60 may be implanted in the patient 20, may remain external to the patient 20, or may have implanted and external portions. The power unit 60 may include a battery 61. The battery 61 is preferably rechargeable and is recharged via a connector 69 to an AC source. Such rechargeable batteries could also be recharged using lead wires or via transcutaneous energy transmission. Optionally, the connector 69 may deliver electrical power to the power unit 60 without the aid of the battery 61. It will be apparent to one of ordinary skill in the art from this disclosure that the control unit 58 can be configured to utilize alternative power-control systems.

Sensors 66 and 67 may be incorporated into the synthetic conduits 17 and 18, the pump 14, or the control unit 58. The sensors 66 and 67 are connected to the control unit 58 via cable 68 or can wirelessly communicate with the control unit 58. The sensors 66 and 67 can monitor blood flow, blood speed, intraluminal pressure, and resistance to flow and may send signals to the control unit 58 to alter pump speed. For example, as the peripheral vein 30 receiving the pumped blood dilates, blood speed in the vein decreases, along with resistance to blood flow 34 from the outflow conduit 18. In order to maintain the desired blood speed and WSS, the pump speed must be adjusted as the peripheral vein 30 dilates over time. The sensors 66 and 67 may sense blood speed in the peripheral vein 30 or resistance to blood flow and then signal the control unit 58 which then increases the speed of the pump 14 accordingly. Thus, the present invention advantageously provides a monitoring system, constituted by the control unit 58 and sensors 66 and 67, to adjust the pump speed to maintain the desired blood speed and WSS in the accepting peripheral vein 30 as it dilates over time. Alternatively, the control unit may rely on a measurement, including an internal measurement of the electrical current to the motor 44 as a basis for estimating blood flow, blood speed, intraluminal pressure, or resistance to flow, thus obviating the need for sensors 66 and 67. The control unit 58 may also include manual controls to adjust pump speed or other pumping parameters.

The control unit 58 is operatively connected to the pump-conduit assembly 12. Specifically, the control unit 58 is operatively connected to the pump 14 by one or more cables 62. Utilizing the power unit 60, the control unit 58 preferably supplies pump motor control current, such as pulse width modulated motor control current to the pump 14 via cable 62. The control unit 58 can also receive feedback or other signals from the pump 14. The control unit 58 further includes a communication unit 64 that is utilized to collect data and communicate the data, via telemetric transmission, for example. Furthermore, the communication unit 64 is configured to receive instructions or data for reprogramming the control unit 58. Therefore, the communication unit 64 is configured to receive instructions or data for controlling the pump 14.

The present invention advantageously provides a monitoring system, constituted by the control unit 58 and sensors 66 and 67, to adjust the operation of the pump to maintain the desired blood speed and WSS in the accepting peripheral vein 30 as it dilates over time.

Preferably, the pump 14 is configured to provide a blood flow 34 in a range from about 50-1500 mL/min, for example, and increase the WSS in an accepting peripheral vein to a range of between 0.76 Pa and 23 Pa, preferably to a range between 2.5 Pa and 7.5 Pa. The pump 14 is configured to maintain the desired level of blood flow and WSS in the accepting peripheral vein 30 for a period of about 7-84 days, for example, and preferably about 14-42 days, for example. In certain situations where a large amount of vein dilation is desired or where vein dilation occurs slowly, the pump 14 is configured to maintain the desired level of blood flow and WSS in the accepting peripheral vein 30 for longer than 42 days.

The pump-conduit assembly 12 can be implanted on the right side of the patient 20, or can be implanted on the left side, as need be. The lengths of the conduits 16 and 18 can be adjusted for the desired placement. Specifically for FIGS. 1B and 1C, the first end 46 of the inflow conduit 16 is fluidly connected to the location 29 in the right internal jugular vein 29 and the first end 52 of the outflow conduit 18 is fluidly connected to the cephalic vein 30 in the right forearm. Specifically for FIGS. 2B and 2C, the first end 46 of the inflow conduit 16 is fluidly connected to the location 29 in the superior vena cava 27 and the first end 52 of the outflow conduit 18 is fluidly connected to the cephalic vein 30 in the right forearm 24. After connection, pumping is started. That is, the control unit 58 begins to operate the motor 44. The pump 14 pumps blood 34 through the outlet conduit 18 and into the peripheral vein 30. The control unit 58 adjusts pumping over the course of time by utilizing data provided by the sensors 66 and 67. FIGS. 1-4 illustrate examples in which the system 10 pumps deoxygenated blood. FIG. 5 illustrates an example in which the system 10 pumps oxygenated blood. In some embodiments, the blood is pumped into the accepting vein with a pulsatility that is reduced when compared with the pulsatility of blood in a peripheral artery. For example, the mean pulse pressure in the accepting vein is <40 mmHg, <30 mmHg, <20 mmHg, <10 mmHg, or preferably <5 mmHg with the pump operating and delivering blood into the peripheral vein. In other embodiments, the blood is pumped into the accepting vein with a pulsatility that is equal to or increased when compared with the pulsatility of blood in a peripheral artery. For these embodiments, the mean pulse pressure in the accepting vein adjacent to the connection with the outflow conduit is ≥40 mmHg with the pump operating.

In one specific embodiment illustrated in FIGS. 1B and 1C, the donating vein 29 is a jugular vein 21, preferentially an internal jugular vein 21. The internal jugular vein 21 is particularly useful as a donating vein 29 due to the absence of valves between the internal jugular vein 21 and the right atrium 31, which would allow the synthetic inflow conduit 16 to be able to draw a large volume of deoxygenated blood per unit time. The inflow conduit 18 is fluidly connected to the internal jugular vein 21 of the patient 20. Deoxygenated blood is drawn from the internal jugular vein 21 and pumped into the peripheral accepting vein 30 in the arm 24 or leg 26 resulting in an increase in the speed of blood 34 and WSS in the peripheral accepting vein. In some embodiments, the blood is pumped into the accepting vein with a pulsatility that is reduced when compared with the pulsatility of blood in a peripheral artery. For example, the mean pulse pressure in the accepting vein adjacent to the connection with the outflow conduit is <40 mmHg, <30 mmHg, <20 mmHg, <10 mmHg, or preferably <5 mmHg with the pump operating.

As noted previously, FIG. 5B illustrates an example in which the system 10 draws oxygenated blood. The inflow conduit 216 is fluidly connected to the radial artery 221 of the patient 20 and the outflow conduit 218 is fluidly connected to the cephalic vein, both using an anastomotic connection. Thus, oxygenated blood is drawn from the radial artery 221 and pumped into the cephalic vein 30 in the arm 24 in a manner that results in an increased blood speed and WSS in the cephalic vein for a sufficient period of time to cause a persistent increase in the overall diameter and lumen diameter of the accepting peripheral vein. In some embodiments, the blood is pumped into the accepting vein with a pulsatility that is reduced when compared with the pulsatility of blood in a peripheral artery. For example, the mean pulse pressure in the accepting vein adjacent to the connection with the outflow conduit is <40 mmHg, <30 mmHg, <20 mmHg, <10 mmHg, or preferably <5 mmHg with the pump operating and delivering blood into the peripheral accepting vein.

Figure 7:
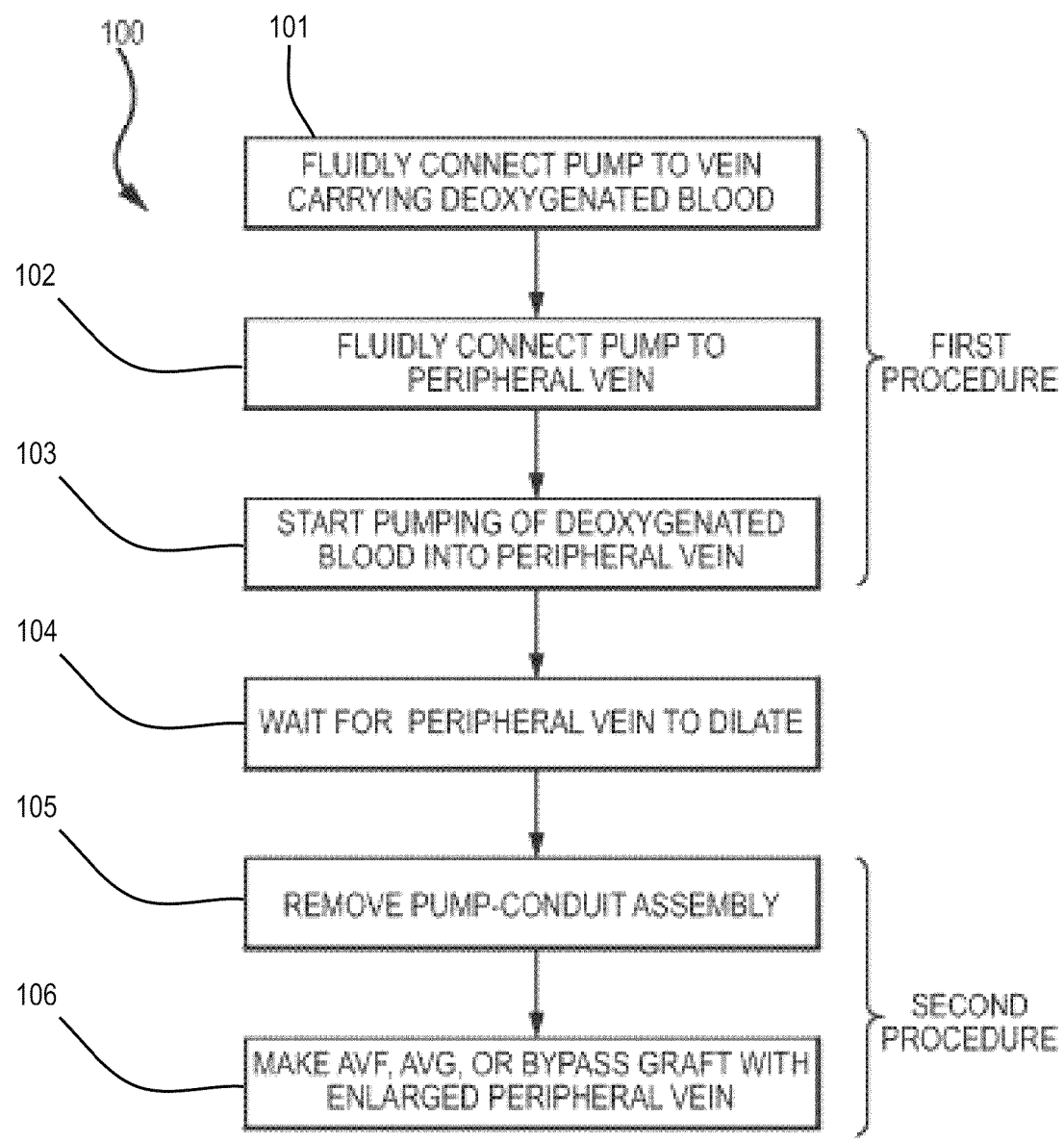
FIG. 7 is a flow chart of a method in accordance with the first and third embodiments of the present invention.
Figure 8:
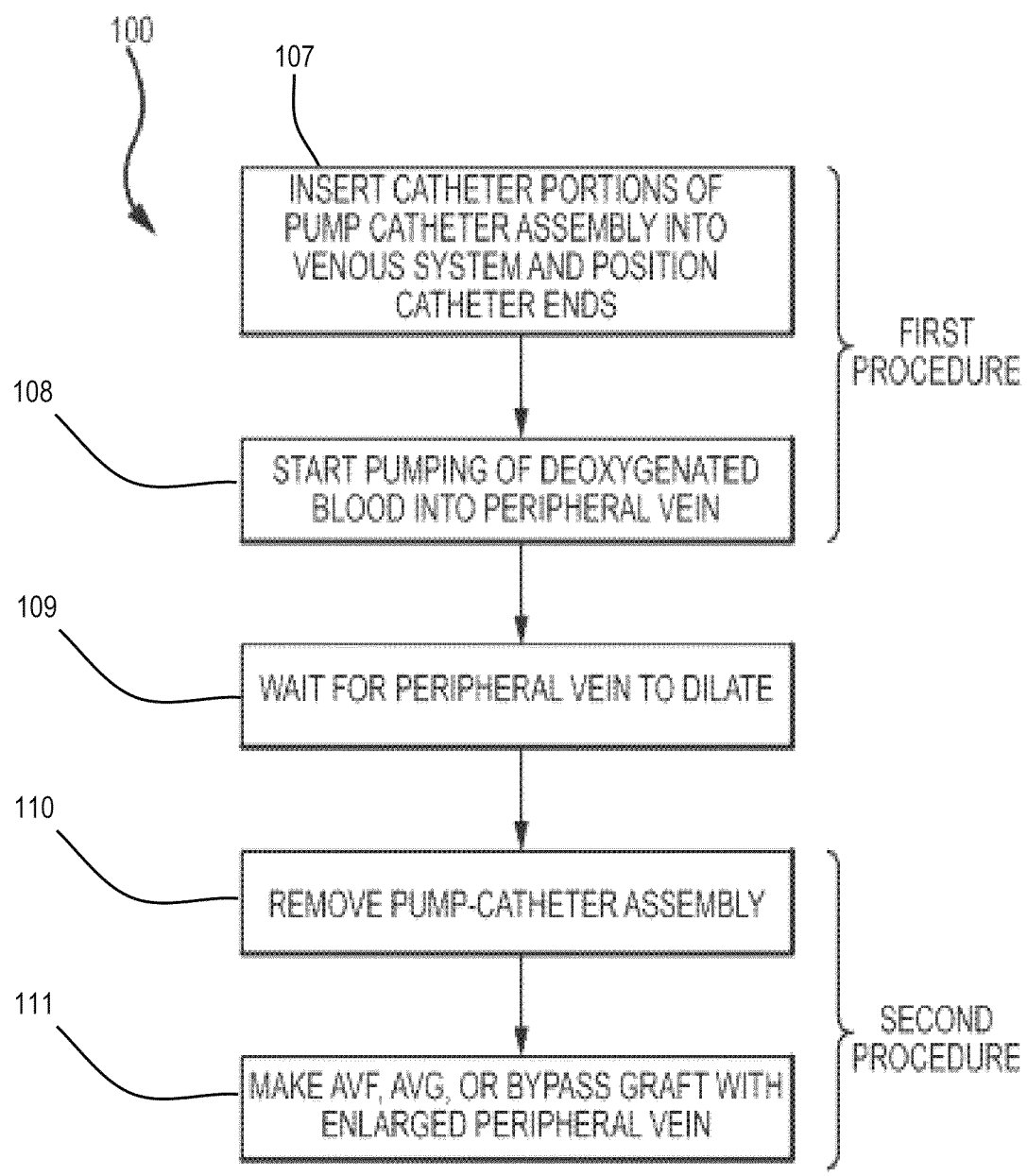
FIG. 8 is a flow chart of a method in accordance with the second and fourth embodiments of the present invention.
Figure 9:
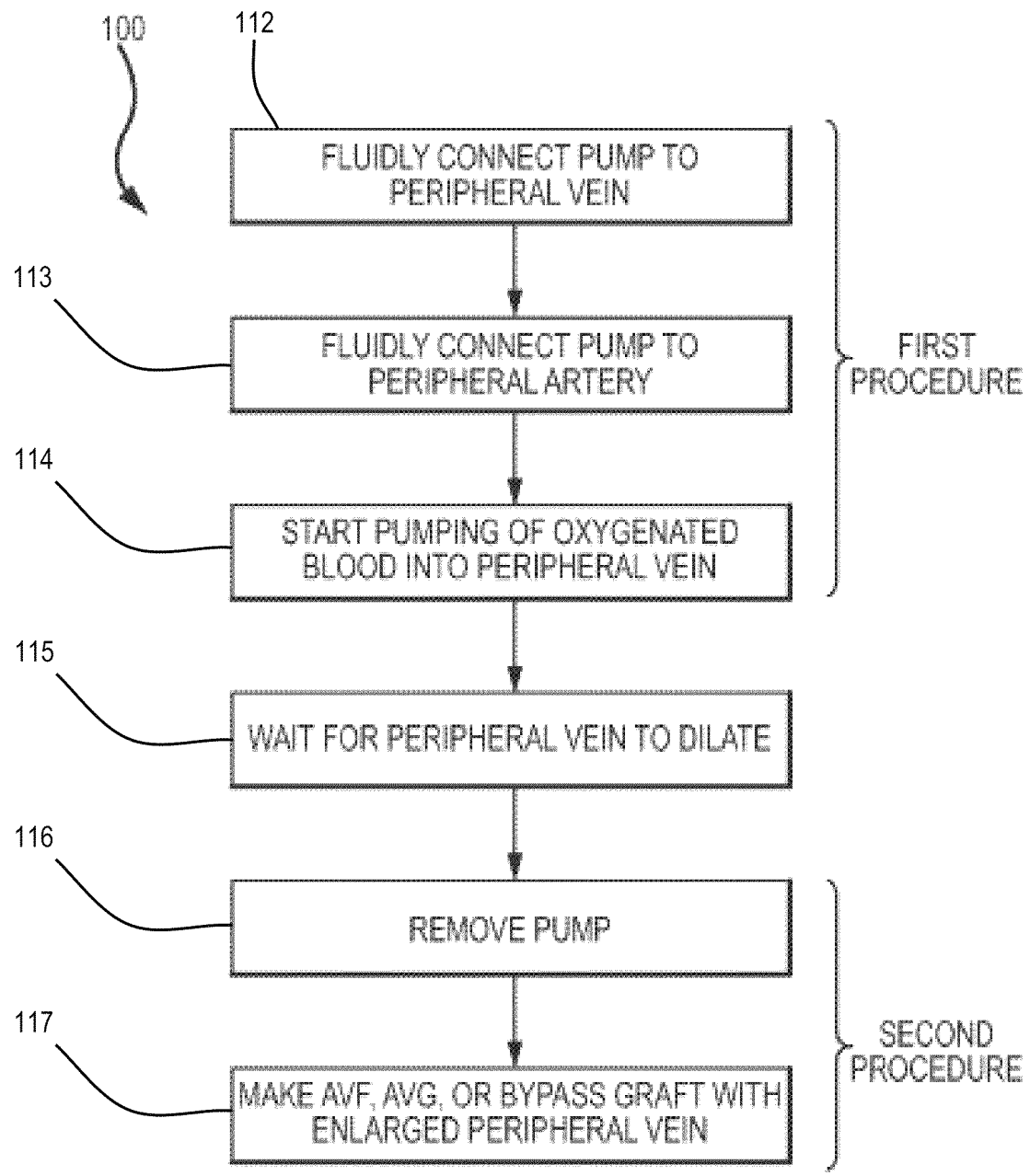
FIG. 9 is a flow chart of a method in accordance with the fifth embodiment of the present invention.

Referring to FIGS. 7-9, various embodiments of the method 100 increase the overall diameter and the lumen diameter of the peripheral vein 30. As shown in FIG. 7, a physician or surgeon performs a procedure to access a vein or artery and connects a pump to establish fluid communication with a vein carrying deoxygenated blood at step 101. At step 102, the pump is connected to a peripheral vein. In this embodiment, the pump-conduit assembly 12 is preferably implanted in the neck, chest and the arm 24 of the patient 20. In another embodiment, wherein the peripheral vein 30 is the saphenous vein 36, the pump-conduit assembly 12 is implanted in the leg 26. In one example, the physician fluidly connects the first end 46 of the pump-conduit assembly 12 to the donating vein 29 and the second end of the pump-conduit assembly 12 to the peripheral accepting vein 30, utilizing a tunneling procedure (as necessary) to connect the two locations subcutaneously. At step 103, the deoxygenated blood is pumped into the peripheral accepting vein. At step 104, the pumping continues for a period of time, while the physician waits for the peripheral accepting vein to dilate. In one embodiment, after the pump is turned on to start the pumping of deoxygenated blood, the skin incisions are closed, as necessary.

In another embodiment, portions of the synthetic conduits 16 and 18 and/or the pump 14 are extracorporeally located. In this embodiment, the pump 14 is then started and controlled via the control unit 58 to pump the deoxygenated blood through the pump-conduit assembly 12 and into the peripheral accepting vein 30 in a manner that increases the blood speed and WSS in the peripheral vein 30. The pumping process is monitored periodically and the control unit 58 is used to adjust the pump 14, in response to changes in the peripheral accepting vein 30. With periodic adjustments, as necessary, the pump continues to operate for an amount of time sufficient to result in the persistent dilation of the overall diameter and lumen diameter of the peripheral vein 30. In a subsequent procedure, the pump-conduit assembly 12 is disconnected and removed at step 105. At step 106, the persistently dilated peripheral vein 30 is used to create an AVF, AVG, or bypass graft.

In another embodiment of the method 100, as shown in FIG. 8, the physician or surgeon inserts one or more catheter portions 50 of the pump-catheter assembly into the venous system and positions them in a donating vessel and a peripheral vein 30 at step 107. At step 108, the pump is operated to pump deoxygenated blood into the deoxygenated blood. The physician then waits for the peripheral vessel to dilate at step 109. The pump-catheter assembly is removed and the persistently dilated vein is used to create an AVF, AVG, or bypass graft, at steps 110 and 111, respectively.

FIG. 9 shows, yet another embodiment of the method 100. At step 112, a physician or surgeon performs a procedure to access a vein and connects a pump to establish fluid communication with a peripheral vein. At step 113, the pump is connected to a peripheral artery. The pump is operated, at step 114 to pump oxygenated blood from the peripheral artery to the peripheral vein. At step 115, the pumping continues for a period of time, while the physician waits for the peripheral vein dilate. At step 116, the pump is removed and at step 117, the persistently dilated vein is used to create an AVF, AVG, or bypass graft.

In various embodiments, the method 100 and/or the system 10 may be used to in periodic and/or intermittent sessions, as opposed to continuous treatment. Typically, hemodialysis treatments that may last from 3 to 5 hours are given in a dialysis facility up to 3 times a week. Therefore, various embodiments of the system 10 and method 100 may be used to provide blood pumping treatments on a similar schedule over a 4 to 6 week period. The treatments may be performed in any suitable location, including in an outpatient setting.

In one embodiment, the blood pumping treatment is done intermittently in conjunction with hemodialysis treatments. In this embodiment, a low-flow pump, a standard in-dwelling hemodialysis catheter functioning as an inflow catheter, and a minimally traumatic needle or catheter placed in the peripheral vein to function as an outflow catheter may be used. A number of continuous flow blood pumps operated from a bedside console [e.g. catheter-based VADs and pediatric cardiopulmonary bypass (CPB) or extracorporeal membrane oxygenation (ECMO) pumps] may be easily adapted for use with the method 100.

In various embodiments where the blood pumping occurs through periodic pumping sessions, the access to the blood vessels may also occur through one or more ports or surgically created access sites. By way of example and not limitation, the access may be achieved through a needle, a peripherally inserted central catheter, a tunneled catheter, a non-tunneled catheter, and/or a subcutaneous implantable port.

In another embodiment of the system 10, a low-flow pump is used to increase WSS and blood speed in a blood vessel. The low-flow pump has an inlet conduit fluidly connected to a blood vessel and an outlet conduit fluidly connected to a vein pumps blood from the blood vessel to the vein for a period between about 7 days and 84 day. The low-flow pump pumps blood such that the wall shear stress of the vein ranges between about 0.076 Pa to about 23 Pa. The low-flow pump also includes an adjustment device. The adjustment device may be in communication with a software-based automatic adjustment system or the adjustment device may have manual controls. The inlet conduit and the outlet conduit may range in length from about 10 centimeters to about 107 centimeters.

The present invention also relates to a method of assembling and operating a blood pump system, including various embodiments of the pump-conduit system 10. The method includes attaching a first conduit in fluid communication with the pump-conduit system 10 to an artery and attaching a second conduit in fluid communication with the pump-conduit system to a vein. The pump-conduit system 10 is then activated to pump blood between the artery and the vein.

In understanding the scope of the present invention, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having", and their derivatives. The terms of degree such as "substantially", "about" and "approximate" as used herein mean a reasonable amount of deviation of the modified term such that the end result is not significantly changed. For example, these terms can be construed as including a deviation of at least ±5% of the modified term if this deviation would not negate the meaning of the word it modifies.

While only selected embodiments have been chosen to illustrate the present invention, it will be apparent to those skilled in the art from this disclosure that various changes and modifications can be made herein without departing from the scope of the invention as defined in the appended claims. For example, the size, shape, location, or orientation of the various components can be changed as needed and/or desired. Components that are shown directly connected or contacting each other can have intermediate structures disposed between them. The functions of one element can be performed by two, and vice versa. The structures and functions of one embodiment can be adopted in another embodiment. It is not necessary for all advantages to be present in a particular embodiment at the same time. Every feature that is unique from the prior art, alone or in combination with other features, also should be considered a separate description of further inventions by the applicant, including the structural and/or functional concepts embodied by such features. Thus, the foregoing descriptions of the embodiments according to the present invention are provided for illustration only, and not for limiting the invention as defined by the appended claims and their equivalents.

What is claimed is:

1. A method for creating an arteriovenous fistula or an arteriovenous graft in a human patient, the method comprising:
   fluidly connecting one end of a pump-conduit assembly to a donating vein;
   fluidly connecting another end of the pump-conduit assembly to an accepting vein;
   pumping deoxygenated blood from the donating vein into the accepting vein for at least 7 days, wherein:
   a) the pumping of blood results in a wall shear stress in the accepting vein of greater than or equal to 0.76 Pa,
   b) the pumping of blood results in a mean pulse pressure in the accepting vein of less than 20 mmHg, and
   c) the pumping of blood results in an increase in overall diameter of the peripheral vein which persists after pumping has ceased and the pump-conduit assembly has been removed; and,
   creating the arteriovenous fistula or arteriovenous graft in the patient using at least a portion of the accepting vein with the persistently-increased overall diameter.

2. The method of claim 1, wherein the patient is in need of an arteriovenous fistula or arteriovenous graft for hemodialysis.

3. The method of claim 1, wherein the pump-conduit assembly pumps blood at a rate between 50 ml/min and 1500 ml/min.

4. The method of claim 1, wherein the pump-conduit assembly pumps blood at a rate between 100 ml/min and 1000 ml/min.

5. The method of claim 1, wherein a wall shear stress in the accepting vein is between 0.76 Pa and 23 Pa when the pump-conduit assembly is in operation.

6. The method of claim 1, wherein a wall shear stress in the accepting vein is between 2.5 Pa and 10 Pa when the pump-conduit assembly is in operation.

7. The method of claim 1, wherein a speed of the blood in the accepting vein is between 15 cm/s and 100 cm/s when the pump-conduit assembly is in operation.

8. The method of claim 1, wherein blood is pumped through the pump-conduit assembly for between 7 days and 42 days.

9. The method of claim 1 further comprising:
   determining the overall diameter of the accepting vein and blood flow through the accepting vein after pumping the blood; and,
   changing a speed of a pump portion of the pump-conduit assembly in order to maintain a desired wall shear stress or blood speed in the accepting vein.

10. The method of claim 1, wherein a pulse pressure of the blood in the accepting vein adjacent to a connection between the accepting vein and the pump-conduit assembly is less than 10 mmHg when the pump-conduit assembly is in operation.

11. The method of claim 1, wherein a pulse pressure of the blood in the accepting vein adjacent to a connection between the accepting vein and the pump-conduit assembly is less than 5 mmHg when the pump-conduit assembly is in operation.

12. The method of claim 1, wherein the blood is pumped through the pump-conduit assembly for a distance of between 20 cm and 200 cm.

13. The method of claim 1, wherein the donating vein is selected from a group consisting of a right atrium, a superior vena cava, an inferior vena cava, a brachiocephalic vein, a jugular vein, a subclavian vein, an axillary vein, a common iliac vein, an external iliac vein, or a femoral vein.

14. The method of claim 1, wherein the accepting vein is selected from a group consisting of a cephalic vein, an ulnar vein, an antecubital vein, a basilic vein, a brachial vein, a lesser saphenous vein, a greater saphenous vein, or a femoral vein.

15. The method of claim 1, wherein a pump portion of the pump-conduit assembly is implanted in the patient.

16. The method of claim 1, wherein a pump portion of the pump-conduit assembly remains extracorporeal to the patient.

17. The method of claim 1, wherein the persistently-increased overall diameter of the accepting vein is at least 2.5 mm.

18. The method of claim 1, wherein the persistently-increased overall diameter of the accepting vein is at least 4.0 mm.

19. The method of claim 1, wherein a pulse pressure of the blood in the accepting vein adjacent to a connection between the accepting vein and the pump-conduit assembly is less than 5 mmHg when the pump-conduit assembly is in operation.

* * * * *